United States Patent
Batra et al.

(10) Patent No.: US 11,236,035 B2
(45) Date of Patent: Feb. 1, 2022

(54) SALTS OF TREPROSTINIL

(71) Applicant: United Therapeutics Corporation, Silver Spring, MD (US)

(72) Inventors: Hitesh Batra, Herndon, VA (US); Vijay Sharma, Olney, MD (US); Sanmin Yang, Oakton, VA (US); Yi Zhang, Burke, VA (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

(21) Appl. No.: 17/107,643

(22) Filed: Nov. 30, 2020

(65) Prior Publication Data

US 2021/0179528 A1 Jun. 17, 2021

Related U.S. Application Data

(63) Continuation of application No. 16/399,682, filed on Apr. 30, 2019, now abandoned, which is a continuation of application No. 15/995,372, filed on Jun. 1, 2018, now abandoned, which is a continuation of application No. 15/614,801, filed on Jun. 6, 2017, now Pat. No. 9,988,334, which is a continuation of application No. 15/359,941, filed on Nov. 23, 2016, now Pat. No. 9,701,611, which is a continuation of application No. 14/634,131, filed on Feb. 27, 2015, now abandoned, which is a continuation of application No. 14/202,618, filed on Mar. 10, 2014, now abandoned.

(60) Provisional application No. 61/791,015, filed on Mar. 15, 2013.

(51) Int. Cl.
C07C 51/41 (2006.01)
C07C 59/72 (2006.01)

(52) U.S. Cl.
CPC .......... C07C 51/41 (2013.01); C07C 51/412 (2013.01); C07C 59/72 (2013.01)

(58) Field of Classification Search
CPC ........ C07C 51/41; C07C 51/412; C07C 59/72
See application file for complete search history.

(56) References Cited

U.S. PATENT DOCUMENTS

| | | | |
|---|---|---|---|
| 4,306,075 | A | 12/1981 | Aristoff |
| 5,153,222 | A | 10/1992 | Tadepalli et al. |
| 5,234,953 | A | 8/1993 | Crow et al. |
| 6,054,486 | A | 4/2000 | Crow et al. |
| 6,441,245 | B1 | 8/2002 | Moriarty et al. |
| 6,521,212 | B1 | 2/2003 | Cloutier et al. |
| 6,528,688 | B2 | 3/2003 | Moriarty et al. |
| 6,700,025 | B2 | 3/2004 | Moriarty et al. |
| 6,756,033 | B2 | 6/2004 | Cloutier et al. |
| 6,756,117 | B1 | 6/2004 | Barnes |
| 6,803,386 | B2 | 10/2004 | Shorr et al. |
| 6,809,223 | B2 | 10/2004 | Moriarty et al. |

(Continued)

FOREIGN PATENT DOCUMENTS

| WO | WO 00/057701 A1 | 10/2000 |
|---|---|---|
| WO | WO 2012/009816 A1 | 1/2012 |
| WO | WO 2012/088607 A1 | 7/2012 |

OTHER PUBLICATIONS

U.S. Appl. No. 14/200,575, filed Mar. 7, 2014, Phares et al.

(Continued)

*Primary Examiner* — Deborah D Carr
(74) *Attorney, Agent, or Firm* — Foley & Lardner LLP

(57) ABSTRACT

Provided are novel treprostinil salts as well as methods for making treprostinil salts.

15 Claims, 4 Drawing Sheets

(56) References Cited

U.S. PATENT DOCUMENTS

| | | |
|---|---|---|
| 7,199,157 B2 | 4/2007 | Wade et al. |
| 7,384,978 B2 | 6/2008 | Phares et al. |
| 7,417,070 B2 | 8/2008 | Phares et al. |
| 7,879,909 B2 | 2/2011 | Wade et al. |
| 7,999,007 B2 | 8/2011 | Jeffs et al. |
| 8,232,316 B2 | 7/2012 | Phares et al. |
| 8,242,305 B2 | 8/2012 | Batra et al. |
| 8,252,839 B2 | 8/2012 | Phares et al. |
| 8,349,892 B2 | 1/2013 | Phares |
| 8,350,079 B2 | 1/2013 | Walsh |
| 8,410,169 B2 | 4/2013 | Phares et al. |
| 8,461,393 B2 | 6/2013 | Sharma |
| 8,481,782 B2 | 7/2013 | Batra et al. |
| 8,497,393 B2 | 7/2013 | Batra et al. |
| 8,536,363 B2 | 9/2013 | Phares et al. |
| 8,563,614 B2 | 10/2013 | Wade et al. |
| 8,609,728 B2 | 12/2013 | Rothblatt et al. |
| 8,653,137 B2 | 2/2014 | Jeffs et al. |
| 8,658,694 B2 | 2/2014 | Jeffs et al. |
| 2005/0165111 A1 | 7/2005 | Wade et al. |
| 2008/0200449 A1 | 8/2008 | Olschewski et al. |
| 2008/0280986 A1 | 11/2008 | Wade et al. |
| 2009/0036465 A1 | 2/2009 | Roscigno et al. |
| 2009/0124697 A1 | 5/2009 | Cloutier et al. |
| 2009/0163738 A1 | 6/2009 | Batra et al. |
| 2010/0076083 A1 | 3/2010 | Olschewski et al. |
| 2012/0190888 A1 | 7/2012 | Batra et al. |
| 2012/0197041 A1 | 8/2012 | Batra et al. |
| 2012/0216801 A1 | 8/2012 | Olschewski et al. |
| 2013/0261187 A1 | 10/2013 | Phares et al. |

OTHER PUBLICATIONS

U.S. Appl. No. 14/223,035, filed Mar. 24, 2014, Batra et al.
Declaration Under 37 CFR 1.132 of Kenneth Phares filed on Aug. 22, 2011, in U.S. Appl. No. 11/189,072.
Declaration Under 37 CFR 1.132 of Kenneth Phares filed on Dec. 22, 2011, in U.S. Appl. No. 12/078,955.
Greene, TW, et al., "Protecting Groups," 1991, 1-11.
Moriarty et al., "The Intramolecular Asymmetric Pauson-Khand Cyclization as a Novel and General Stereoselective Route to Benzindene Prostacyclins: Synthesis of UT-15 (Treprostinil)," *J. Org. Chem.* 2004, 69, 1890-1902.

SALTS OF TREPROSTINIL

CROSS-REFERENCE TO RELATED APPLICATIONS

This application is a Continuation of U.S. application Ser. No. 16/399,682, filed Apr. 30, 2019, which is a Continuation of U.S. application Ser. No. 15/995,372, filed Jun. 1, 2018, which is a Continuation of U.S. application Ser. No. 15/614,801, filed Jun. 6, 2017, now U.S. Pat. No. 9,988,334, which is a Continuation of U.S. application Ser. No. 15/359,941, filed Nov. 23, 2016, now U.S. Pat. No. 9,701,611, which is a Continuation of U.S. application Ser. No. 14/634,131, filed Feb. 27, 2015, which is a Continuation of U.S. application Ser. No. 14/202,618, filed Mar. 10, 2014, now abandoned, which claims the benefit under 35 U.S.C. § 119(e) of U.S. Provisional Application No. 61/791,015, filed on Mar. 15, 2013, the contents of which are hereby incorporated by reference in their entirety into the present disclosure.

BACKGROUND

Treprostinil, the active ingredient in Remodulin®, Tyvaso® and Orenitram™, was first described in U.S. Pat. No. 4,306,075. Treprostinil, and other prostacyclin derivatives may be prepared as described in Moriarty, et al in *J. Org. Chem.* 2004, 69, 1890-1902, *Drug of the Future*, 2001, 26(4), 364-374, U.S. Pat. Nos. 6,441,245, 6,528,688, 6,700,025, 6,809,223, 6,756,117; 8,461,393; 8,481,782; 8,242,305; 8,497,393; US patent applications nos. 2012-0190888 and 2012-0197041; PCT publication no. WO2012/009816.

Various uses and/or various forms of treprostinil are disclosed, for examples, in U.S. Pat. Nos. 5,153,222; 5,234,953; 6,521,212; 6,756,033; 6,803,386; 7,199,157; 6,054,486; 7,417,070; 7,384,978; 7,879,909; 8,563,614; 8,252,839; 8,536,363; 8,410,169; 8,232,316; 8,609,728; 8,350,079; 8,349,892; 7,999,007; 8,658,694; 8,653,137; US patent application publications nos. 2005/0165111; 2009/0036465; 2008/0200449; 2010-0076083; 2012-0216801; 2008/0280986; 2009-0124697; 2013-0261187; PCT publication no. WO00/57701; US provisional applications nos. 61/781,303 filed Mar. 14, 2013 and 61/805,048 filed Mar. 25, 2013. The teachings of the aforementioned references are incorporated by reference to show how to practice the embodiments of the present invention.

The teachings of the aforementioned references are incorporated by reference to show how to practice the embodiments of the present invention. The methods described in these documents, however, do not describe a feasible production method for producing salts of treprostinil because the methods require the use of excessive amounts of reagents and tedious chromatographic purification techniques. Therefore, there is a need for an economical, efficient and simplified method for preparing salts of treprostinil.

In sum, treprostinil is of great importance from a medicinal point of view. Therefore, a need exists for stable forms of treprostinil which presents advantage in storage, shipment, handling, and/or formulation, for example. From synthetic point of view, the desired properties of UT-15 salts may include one or more of the following properties: better aqueous solubility, higher melting point, dense nature, and robust process.

SUMMARY

Certain embodiments of the present invention relate to methods of preparing various salts of treprostinil.

One embodiment provides a treprostinil salt compound according to the following formula:

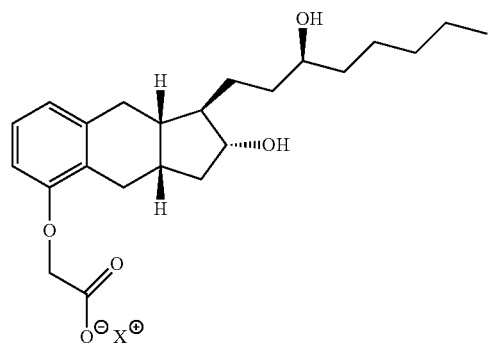

that may be optionally produced by a process comprising: alkylating a starting compound of the formula:

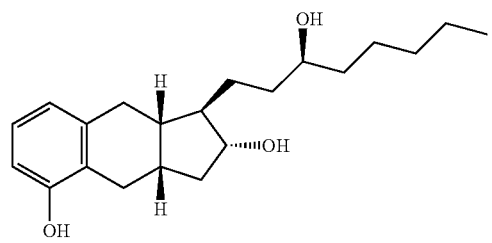 [SMILES: CCCCC[C@H](O)CC[C@@H]1[C@H]2Cc3cccc(O)c3C[C@H]2C[C@H]1O]

to form an O-alkylated compound that is not isolated; followed by optional base hydrolysis and contacting the resulting compound with a base or a base salt in situ; wherein X is a pharmaceutically acceptable salt counterion and the treprostinil salt is isolated as at least 98% pure. In one embodiment, the treprostinil salt comprises Group IA or IIA metal. In another embodiment, the treprostinil salt comprises K, Ca, Na, Ba, Li, Mg, or Cs. In yet another embodiment, the treprostinil salt as isolated is at least 98.5% pure; at least 98.8% pure; at least 99% pure; at least 99.1% pure; at least 99.2% pure; at least 99.3% pure; at least 99.4% pure; at least 99.5% pure; at least 99.6% pure; at least 99.7% pure; at least 99.8% pure or at least 99.9% pure.

One embodiment provides a treprostinil salt compound according to the following formula:

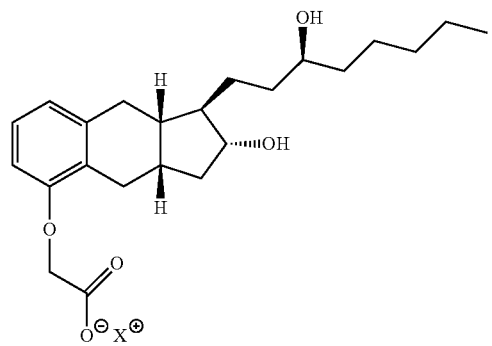

wherein X is a pharmaceutically acceptable salt counterion and the treprostinil salt is isolated preferably in a crystalline form. Preferably, the isolated salt is at least 99% pure. In one embodiment, the treprostinil salt comprises a Group IA or IIA metal. In another embodiment, the treprostinil salt comprises K, Ca, Na, Ba, Li, Mg or Cs. In yet another embodiment, the treprostinil salt as isolated is at least 99.1% pure; at least 99.2% pure; at least 99.3% pure; at least 99.4% pure; at least 99.5% pure; at least 99.6% pure; at least 99.7% pure; at least 99.8% pure or at least 99.9% pure or at least 99.95% pure.

One embodiment provides a treprostinil salt compound according to the following formula:

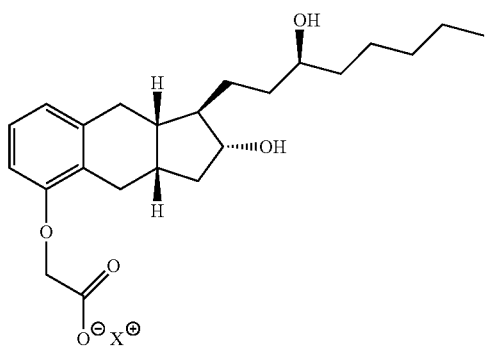

that may be optionally produced by a process comprising: alkylating a starting compound of the formula:

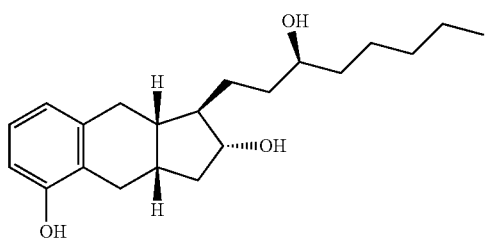 [SMILES: CCCCC[C@H](O)CC[C@@H]1[C@H]2Cc3cccc(O)c3C[C@H]2C[C@H]1O]

to form an O-alkylated compound that is not isolated; followed by hydrogenolysis and contacting the resulting compound with a base or a base salt in situ; wherein X is a pharmaceutically acceptable salt counterion and the treprostinil salt is isolated as at least 98% pure. In one embodiment, the treprostinil salt comprises a Group IA or IIA metal. In another embodiment, the treprostinil salt comprises K, Ca, Na, Ba, Li, Mg or Cs. In yet another embodiment, the treprostinil salt as isolated is at least 98.5% pure; at least 98.8% pure; at least 99% pure; at least 99.1% pure; at least 99.2% pure; at least 99.3% pure; at least 99.4% pure; at least 99.5% pure; at least 99.6% pure; at least 99.7% pure; at least 99.8% pure or at least 99.9% pure.

Another embodiment provides a method for making a treprostinil salt compound according to the following formula:

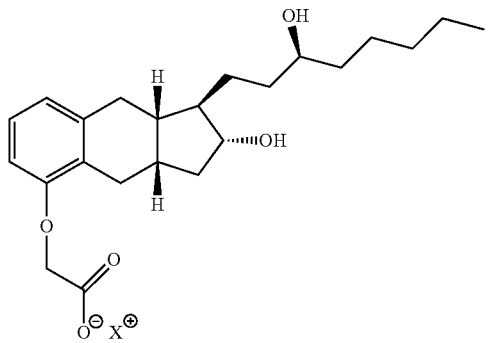

comprising alkylating a starting compound of the formula:

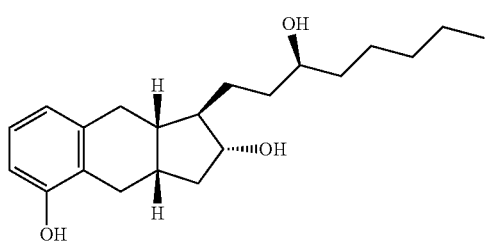 [SMILES: CCCCC[C@H](O)CC[C@@H]1[C@H]2Cc3cccc(O)c3C[C@H]2C[C@H]1O]

to form an O-alkylated compound that is not isolated; followed by optional base hydrolysis and contacting the resulting compound with a base or a base salt in situ; wherein X is a pharmaceutically acceptable salt counterion and the treprostinil salt is isolated as at least 98% pure. In one embodiment, the treprostinil salt comprises a Group IA or IIA metal. In another embodiment, the treprostinil salt comprises K, Ca, Na, Ba, Li, Mg or Cs. In yet another embodiment, the treprostinil salt as isolated is at least 98.5% pure; at least 98.8% pure; at least 99% pure; at least 99.1% pure; at least 99.2% pure; at least 99.3% pure; at least 99.4% pure; at least 99.5% pure; at least 99.6% pure; at least 99.7% pure; at least 99.8% pure or at least 99.9% pure.

Yet another embodiment provides a method for making a treprostinil salt compound according to the following formula:

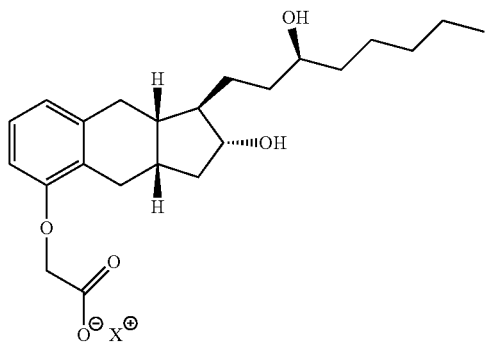

comprising alkylating a starting compound of the formula:

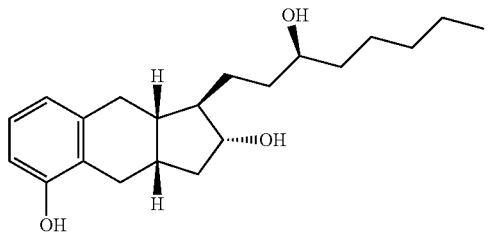 [SMILES: CCCCC[C@H](O)CC[C@@H]1[C@H]2Cc3cccc(O)c3C[C@H]2C[C@H]1O]

to form an O-alkylated compound that is not isolated; followed by hydrogenolysis and contacting the resulting compound with a base or a base salt in situ; wherein X is a pharmaceutically acceptable salt counterion and the treprostinil salt is isolated as at least 98% pure. In one embodiment, the treprostinil salt comprises a Group IA or IIA metal. In another embodiment, the treprostinil salt comprises K, Ca, Na, Ba, Li, Mg or Cs. In yet another embodiment, the treprostinil salt as isolated is at least 98.5% pure; at least 98.8% pure; at least 99% pure; at least 99.1% pure; at least 99.2% pure; at least 99.3% pure; at least 99.4% pure; at least 99.5% pure; at least 99.6% pure; at least 99.7% pure; at least 99.8% pure or at least 99.9% pure.

BRIEF DESCRIPTION OF THE DRAWINGS

In FIG. 1 each of R1 and R2 may be independently selected from H or an alcohol protecting group, such as H, TBDMS, THP, substituted or unsubstituted benzyl group. Exemplary alcohol protecting groups include, but are not limited to, actetyl, benzoyl, benzyl, p-methoxyethoxymethyl ether, methoxymethyl ether, dimethoxytrityl, p-methoxybenzyl ether, trityl, silyl ether (e.g., trimethylsilyl (TMS), tert-butyldimethylsilyl (TBMDS), tert-butyldimethylsilyloxymethyl (TOM) or triisopropylsilyl (TIPS) ether), tetrahydropyranyl (THP), methyl ether and ethoxyethyl ether (EE).

DETAILED DESCRIPTION

Unless otherwise specified, "a" or "an" means "one or more". The present invention relates to a novel monohydrate form of treprostinil. Treprostinil is the active ingredient of Remodulin®, which has been approved by the U.S. FDA for the treatment of Pulmonary Arterial Hypertension (PAH) in patients with NYHA Class II, III and IV symptoms to diminish symptoms associated with exercise using subcutaneous or intravenous administration. Treprostinil is also the active ingredient in Tyvaso® inhalation solution and Orenitram™ extended-release tablets.

Treprostinil's chemical name is 2-((1R,2R,3aS,9aS)-2-hydroxy-1-((S)-3-hydroxyoctyl)-2,3,3a,4,9,9a-hexahydro-1H-cyclopenta[b]naphthalen-5-yloxy)acetic acid of the following structure:

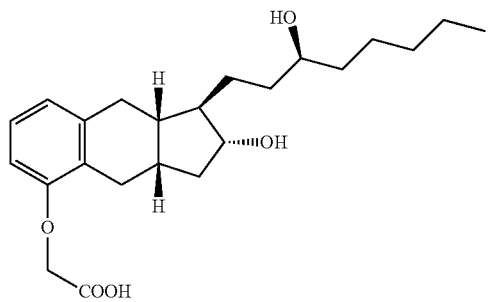 [SMILES: CCCCC[C@H](O)CC[C@@H]1[C@H]2Cc3cccc(OCC(=O)O)c3C[C@H]2C[C@H]1O]

Figure 1:
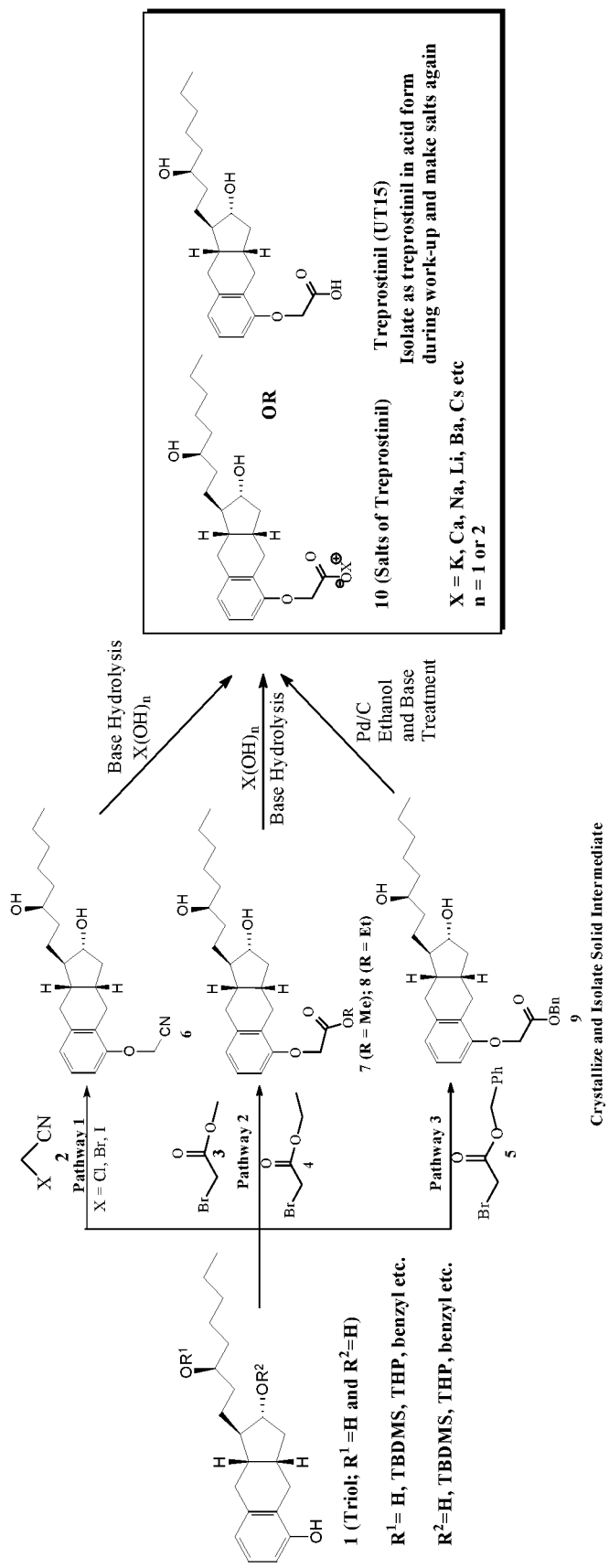
FIG. 1 shows embodiments of exemplary synthetic pathways which result in treprostinil salt.

Treprostinil (UT-15) is a benzindene prostacyclin containing carboxylic acid functionality, various bases and base salts may react with the acid functionality to form new salts of treprostinil as shown in FIG. 1. In some embodiments, a hydroxide base, such as alkaline metal hydroxide, may be reacted with treprostinil or a synthetic intermediate of treprostinil to form a salt of treprostinil. The hydroxide base may be, for example, an inorganic base such as ammonium hydroxide, potassium hydroxide, calcium hydroxide, sodium hydroxide, barium hydroxide, cesium hydroxide, lithium hydroxide and magnesium hydroxide. The resulting salt may be, for example, Potassium, Calcium, Sodium, Barium, Lithium, Magnesium or Cesium salt. Yet in some embodiments, a base salt, such as a carbonate, may be reacted with treprostinil or a synthetic intermediate of treprostinil to form a salt of treprostinil. The carbonate may be, for example, lithium carbonate, potassium carbonate, sodium carbonate, cesium carbonate, calcium carbonate, ammonium carbonate.

Additional salts may be used according to the processes embodied herein, including for example, compounds with basic groups, such as amine groups, basic salts include ammonium salts, alkali metal salts (such as sodium, potassium and cesium salts) and alkaline earth metal salts (such as magnesium, calcium and barium salts).

One embodiment includes synthesis of a form new salt of treprostinil by any of the following methods. In some embodiments, the synthesis of salt may be a two step process starting from compound of formula (1)

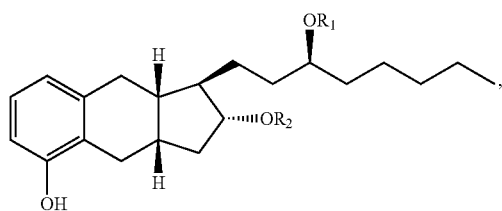

(1)

wherein each of R1 and R2 may be independently selected from H or an alcohol protecting group, such as H, TBDMS, THP, substituted or unsubstituted benzyl group. As used herein, "an alcohol protecting group" is a functional group that protects the alcohol group from participating in reactions that are occurring in other parts of the molecule. Suitable alcohol protecting groups are well known to those of ordinary skill in the art and include those found in T. W. Greene, *Protecting Groups in Organic Synthesis*, John Wiley & Sons, Inc. 1981, the entire teachings of which are incorporated herein by reference. Exemplary alcohol protecting groups include, but are not limited to, actetyl, benzoyl, benzyl, p-methoxyethoxymethyl ether, methoxymethyl ether, dimethoxytrityl, p-methoxybenzyl ether, trityl, silyl ether (e.g., trimethylsilyl (TMS), tert-butyldimethylsilyl (TBMDS), tert-butyldimethylsilyloxymethyl (TOM) or tri-isopropylsilyl (TIPS) ether), tetrahydropyranyl (THP), methyl ether and ethoxyethyl ether (EE). In many embodiments, the starting material may be benzindene triol, i.e. compound of formula (1) with both $R_1$ and $R_2$ being H.

The first step may be alkylating compound of formula (1), such benzindene triol, with an alkylating reagent. In some embodiments, the alkylating reagent may have formula

wherein X may be a halogen, such as Cl, Br or I; R may be CN or COOR', wherein R' may be an alkyl group or substituted or unsubstituted benzyl. An alkyl group may be a saturated straight-chain or branched aliphatic group. For example, an alkyl group may a (C1-C6)alkyl, (C1-C5)alkyl, (C1-C4)alkyl or (C1-C3)alkyl. Examples of alkyl groups include methyl, ethyl, n-propyl, isopropyl, n-butyl, isobutyl, sec-butyl, tert-butyl, pentyl, iso-amyl, and hexyl. An alkyl group is optionally substituted with an alkyl, a cycloalkyl (e.g., cyclopentyl or cyclohexyl), an aryl (e.g., phenyl), or heteroaryl group. A substituted benzyl group may be optionally substituted at one or more meta, ortho or para positions with one or more substituents, which may be independently selected from the group consisting of —$NO_2$, —CN, halogen (e.g., —F, —Cl, —Br or —I), (C1-C3)alkyl, halo(C1-C3)alkyl, (C1-C3)alkoxy and halo(C1-C3)alkoxy. In certain embodiments, the substituted benzyl group may be para-methoxy benzyl or para-nitrobenzyl.

As the result of the alkylating step, the following compound of formula (2) may be formed:

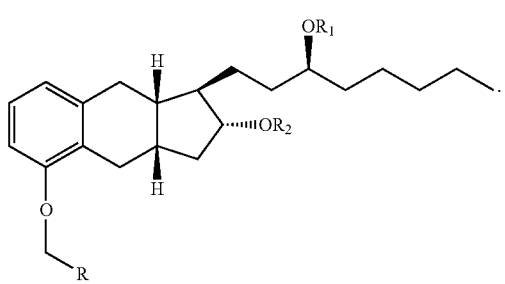

(2)

In some embodiments, the alkylating step may be performed in the present of a base or a base salt, which may be, for example, lithium carbonate, potassium carbonate, sodium carbonate, cesium carbonate, calcium carbonate, ammonium carbonate, lithium hydroxide, potassium hydroxide, magnesium hydroxide, barium hydroxide, sodium hydroxide, calcium hydroxide.

In some embodiments, a solvent for the alkylating step may be a polar aprotic solvent such as acetone, butanone, tetrahydrofuran, tetriarybutyl methyl ether, ethyl acetate or a combination thereof.

In some embodiments, the alkylating step may be performed without a catalyst. Yet in some other embodiments, the alkylating step may be performed in the presence of an alkylation catalyst, which may be, for example, tetrabutyl ammonium bromide, potassium iodide or sodium iodide.

In some embodiments, the second step may be hydrolysis of the product of the alkylating step, such as compound of formula 2. In certain embodiments, the hydrolysis may be followed by isolation and/or crystallization of the product of hydrolysis from an appropriate solvent. The product of hydrolysis may be treprostinil salt

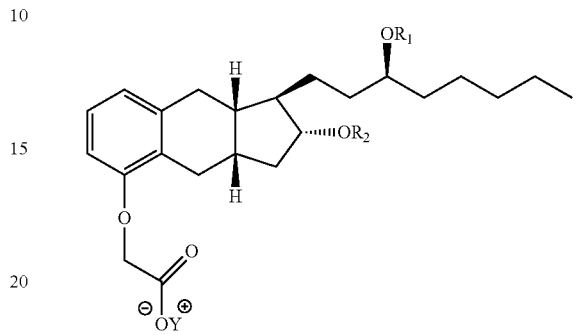

or treprostinil as a free acid. The hydrolysis may be performed by reacting the product of the alkylating step, such as compound of formula 2, with a solution, which may comprise one or more of hydroxide or a basic salt, such as carbonate. The hydroxide may be, for example, ammonia hydroxide or a metal hydroxide. The metal hydroxide may be, for example, a hydroxide of Group IA or Group IIA solution. In certain embodiments, the metal hydroxide may be a hydroxide of K, Ca, Mg, Ba, Cs, Li or Na. In some embodiments, the basic salt may be, for example, a carbonate, such as lithium carbonate, potassium carbonate, sodium carbonate, cesium carbonate, calcium carbonate or ammonium carbonate.

In some cases, a solvent for the hydrolysis and a solvent for the isolation and/or crystallization step may the same, but in other cases, they may be different. Such solvent(s) may be an organic solvent selected from ethanol, isopropyl alcohol, methanol, acetone, ethyl acetate, hexanes, heptanes, isopropyl acetate or combinations thereof.

In some embodiments, when R' is substituted or unsubstituted benzyl group, the second step may be hydrogenalyzation of the alkylation product, such as compound of formula 2. The hydrogenalyzation of the alkylation product may be performed using a hydrogenation catalyst, such as Pd catalyst on Carbon, in presence of hydrogen. The hydrogenalyzation may be performed in an alcoholic solvent, such as ethanol, methanol or isopropyl alcohol. As the result of the hydrogenalyzation, the benzyl group may be cleaved, thereby forming a "raw" mixture comprising treprostinil as a free acid. In some embodiments, the "raw" mixture may be filtered and evaporated to form solid treprostinil. Yet in some embodiments, the raw mixture may be treated with a base, such as a hydroxide, or a base salt, such as a carbonate, to form treprostinil salt, which may be isolated and/or crystallized.

In some embodiments, if treprostinil as a free acid is isolated as an intermediate, it may be then converted to its salt form using an appropriate base or a base salt, which may be one or more of hydroxide or carbonate, such as the ones discussed above. In one embodiment, treprostinil may be formed in situ and contacted with a base or a base salt to form a new salt of treprostinil. In one embodiment, treprostinil is contacted with a base or a base salt to form a new salt of treprostinil.

In some embodiments, the synthesis process may involve passing through multiple, i.e. more than 1, stages for either or both of treprostinil as a free acid and treprostinil salt. For example, as the result of hydrolysis or hydrogenolysis treprostinil as a free acid may be formed, which may be converted to a salt, which then may converted back to treprostinil as a free acid, which may have higher purity that the earlier treprostinil. Also, a formed treprostinil salt may be converted to treprostinil as a free acid, which may be converted to a new salt, which may be the same or different from the original salt. Treprostinil or treprostinil salt during each stage may or may not be isolated and/or crystallized before a subsequent conversion.

FIG. 1 illustrates certain embodiments includes for synthesis treprostinil salts. The synthesis of salt is a two or three step process starting from benzindene triol: 1) the first step is the O-alkylation of benzindene triol (1) with various alkylating reagents as shown in FIG. 1; 2) the second step is the optional hydrolysis of the nitrile intermediate (6) or ester intermediates (7), (8) and (9) by using alkali metal bases followed by isolation and crystallization of the salt from an appropriate solvent such as one of ethanol, isopropyl alcohol, methanol, acetone, ethyl acetate, hexanes, heptanes, isopropyl acetate or a combination thereof. In some cases, the solvent system for both reaction step and recrystallization step are same, but in other cases they may be different; 3) if treprostinil as a free acid is being isolated as an intermediate then convert it back to its salt form using appropriate base as described in FIG. 1. In one embodiment, treprostinil is formed in situ and contacted with the base salt to form the new salt of treprostinil. In one embodiment, treprostinil is contacted with the base salt to form the new salt of treprostinil The methods embodied herein allow for the formation of treprostinil or treprostinil salt with reduced or simplified purification. In one embodiment, treprostinil salt may be formed from compound of formula 1, such as benzindene triol, without any intermediate purification and/or isolation of treprostinil as a free acid. In one embodiment, a composition comprising treprostinil as a free acid and at least one impurity is contacted with the base salt to form the new salt of treprostinil to form a substantially pure new salt of treprostinil. In some embodiments, the new salt of treprostinil is isolated as approximately 99.0, 99.1, 99.2, 99.3, 99.4, 99.5, 99.6, 99.7, 99.8, 99.9 or 99.95 percent pure.

The present salts may have an impurity profile different than treprostinil materials produced by prior art methods. For example, the present salts may have a lower concentration of one or more of treprostinil impurities, such as any of 1AU90, 2AU90 and 3AU90, which are stereoisomers of treprostinil (UT-15); triol (which could be a process impurity or a degradation product); methyl ester and ethyl ester (process impurities), respectively; and 750W93 and 751W93 (two dimers of treprostinil where the acid group of one molecule esterifies with an alcohol on another molecule of UT-15). In some embodiments, the new salt of treprostinil does not comprise one or more of the listed impurities in a detectable amount.

In some embodiments, the methods allow for the production of a substantially pure salt of treprostinil from the triol (1) without intermediate purification steps. The yield of the salt from the triol (1) may be greater than 70%, or greater than 75%, or greater than 80%, or greater than 85%, or greater than 90%.

Pathway 1, Pathway 2 or Pathway 3): Triol (1) may be alkylated using various an alkylating reagent such as

Figure 4:
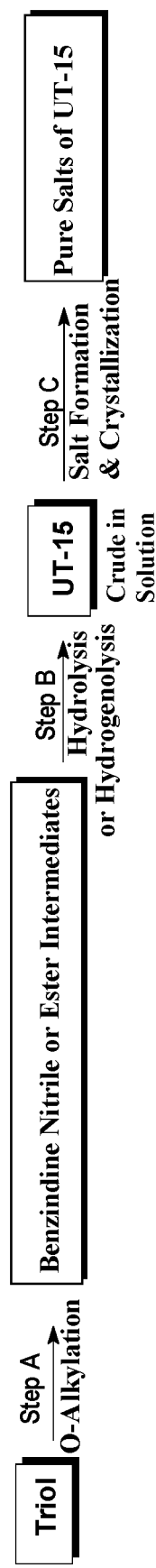
FIG. 4 is a flow chart for synthesis of salts of UT-15 and UT-15 starting from triol.

which may be halo acetonitrile (2), methyl bromoacetate (3), ethyl bromoacetate (4) and benzyl bromoacetate (5) etc. in the presence of a base or base salt, such as potassium carbonate, cesium carbonate, lithium hydroxide etc. The O-alkylation of the phenolic hydroxyl group of triol (1) may be carried out, for example, with 1-1.2 equivalents of the alkylating agent in presence of 1-3 equivalents of the base or a the base salt in a solvent, such as acetone, butanone, tetrahydrofuran, tertiarybutyl methyl ether, ethyl acetate. This O-alkylation may be carried with or without catalyst such as tetrabutyl ammonium bromide, potassium iodide or sodium iodide etc. Alkylation with haloacetonitrile (2) may provide nitrile intermediate (6) which may be carried forward to hydrolysis (step 6→40) without any further chromatographic purification. Similarly, the O-alkylation of triol (1) may be performed using an acetate, such as methyl bromoacetate (3), ethyl bromoacetate (4) and benzyl bromoacetate (5) there by providing ester in the form penultimate intermediates (7, 8 and 9) of treprostinil. These ester intermediates (7, 8 and 9) may be carried forward for hydrolysis without any further chromatographic purification. The ester intermediate 9 bearing a benzyl group may be hydrogenolysed using Palladium catalyst on carbon in presence of hydrogen in an alcoholic solvent, such as ethanol, methanol, and isopropyl alcohol. The whole process may be simplified by the fact that after the benzyl group may cleave during the hydrogenation condition (step 6→40) the alcoholic solution of reaction mixture containing treprostinil (UT-15) in the form of a free acid is filtered and evaporated to obtain treprostinil (UT-15) or this may be treated with) 0.5 to 1 equivalent of a base or a base salt, such as potassium hydroxide, calcium hydroxide, sodium hydroxide, barium hydroxide, cesium hydroxide, lithium hydroxide. This telescoping of the steps may lead to a process as shown in FIG. 4.

In the pathways 1, 2 and 3 the intermediates 6, 7, 8 and 9 after may provide treprostinil or its salt form (10) depending on the base used during hydrolysis and its isolation during the process. The pathways discussed above may be schematically represented as follows:

Pathway 1:

Error! Objects cannot be created from editing field codes.

Experimental Steps may include: 1) O-Alkylate the triol and carry the nitrile intermediate as such without purification to next step for hydrolysis.

2) Hydrolyze the ester intermediate and isolate as a salt form.

3) Crystallize to obtain the pure salt form.

Pathway 2:
Error! Objects cannot be created from editing field codes.

Experimental Steps may include 1) O-Alkylate the triol and carry the ester intermediate as such without purification to next step for hydrolysis. The ester intermediate "R" is not necessarily limited to Me and Et, but rather any suitable ester known in the art may be used. For example, R may be $C_1$-$C_{12}$ alkyl or a $C_1$-$C_6$ alkyl. R may be optionally substituted by one or more organic moieties that are compatible with the conditions of the base hydrolysis step.

2) Hydrolyze the ester intermediate and isolate as salt form.

3) Crystallize to obtain the pure salt form.

Pathway 3:
Error! Objects cannot be created from editing field codes.

Experimental Steps: 1) O-Alkylate the triol and carry the ester intermediate as such without purification to next step for hydrogenolysis.

2) Hydrogenolyze the ester intermediate and carry the alcoholic solution, such as a methanol or ethanol solution, of acid for treatment with base and form the salt. Or the ester may be hydrolyzed with base to obtain the salt form of treprostinil. The benzyl ether may be optionally substituted benzyl. Alternatively, the benzyl may instead be an optionally substituted aryl moiety.

3) Crystallize to obtain the pure salt form.

In one embodiment, the salt of UT-15 demonstrates at least one of the following improved properties: improved solubility, desired biological activity, chemically-stable solid form and a solid form that is stable in a solid-dose formulation.

The present application also provides a number of novel treprostinil salts including potassium salt of treprostinil; !-arginine salt of treprostinil, l-lysine salt of treprostinil, N-methylglucamine salt of treprostinil; choline salt of treprostinil; magnesium salt of treprostinil; ammonium salt of treprostinil; calcium salt of treprostinil and tromethamine salt of treprostinil. In some embodiments, the salt of treprostinil may be in a crystalline solid form. Yet in some embodiments, the salt of treprostinil may in an amorphous solid form. Yet in some embodiments, the salt of treprostinil may be a mixture of at least one crystalline solid form and an amorphous solid form. A purity of the salt in the solid form may be at least 98.0%; at least 98.5%; at least 98.8%; at least 99%; at least 99.1%; at least 99.2%; at least 99.3%; at least 99.4%; at least 99.5%; at least 99.6%; at least 99.7%; at least 99.8%; or at least 99.9% or at least 99.95%. The novel salts may be produced in large quantities, such as of at least 20 g or at least 30 g or at least 40 g or at least 50 g or at least 60 g or at least 70 g or at least 80 g or at least 90 g or at least 100 g or at least 110 g or at least 120 g or at least 130 g or at least 140 g or at least 150 g or at least 160 g or at least 170 g or at least 180 g or at least 190 g or at least 200 g.

One or more salt disclosed in this application may be used for preparing a pharmaceutical formulation together with one or more pharmaceutically acceptable excipient or additive. Suitable additives or excipients include, but not limited to, sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. In some embodiments, while being dissolved in an appropriate solvent one or more salts may be used for preparing a treprostinil formulation for administering via subcutaneous, intravenous, oral or inhalation route.

In some embodiments, one or more of the present salts in a solid form may also be used for preparing a solid dosage oral form, such as a powder, a granule, a tablet, a pellet, a pill, a capsule, a gelcap, and a caplet, for oral administering. Optionally, the oral dosage form may contain one or more other ingredients to aid in administration, such as an inactive diluent, or a lubricant, such as magnesium stearate, or a preservative, such as paraben or sorbic acid, or an antioxidant, such as ascorbic acid, tocopherol or cysteine, a disintegrating agent, a binders, a thickener, a buffer, a sweetener, a flavoring agent or a perfuming agent. Additionally, one or more of dyestuffs or pigments may be added for identification. Tablets may be further treated with suitable coating materials known in the art.

The invention is further illustrated by, though in no way limited to, the following examples.

EXPERIMENTAL EXAMPLES

Example 1: Preparation of UT-15D-Potassium Salt

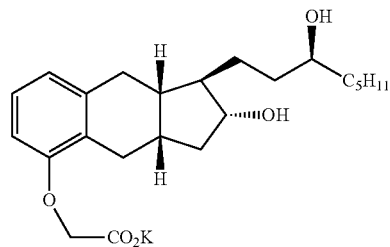

Treprostinil potassium salt was made by adding treprostinil (UT-15) to potassium hydroxide ethanol solution, followed by in two different solvents: acetone or ethyl acetate. The experiment was carried out in each solvent system (ethanol/acetone and ethanol/ethyl acetate) with different ratio to find the best condition to make the target compound. The results showed that ethanol/ethyl acetate is a better solvent system than ethanol/acetone, comparably. As can be seen in the table 1 and 2, when the volume of acetone or ethyl acetate increased, the yield of UT-15 potassium salt also increased accordingly, until the yield reached to the peak at about 80%. Overall, the reaction condition at ethanol/ethyl acetate ratio 1/10 is easy to work with, in term of solvent boiling point, volume and yield of product (~80%). Based on the results of the reaction in ethanol and ethyl acetate, an experiment with a larger scale of ~(40 g) was carried out. The results confirmed the above findings. The melting point of the UT-15 potassium salt was about 180° C. in both ethanol/acetone and ethanol ethyl acetate cases. The structure of UT-15 potassium was confirmed by QC analytical data and other spectral data.

Scheme 1 presents the flow chart of synthesis:

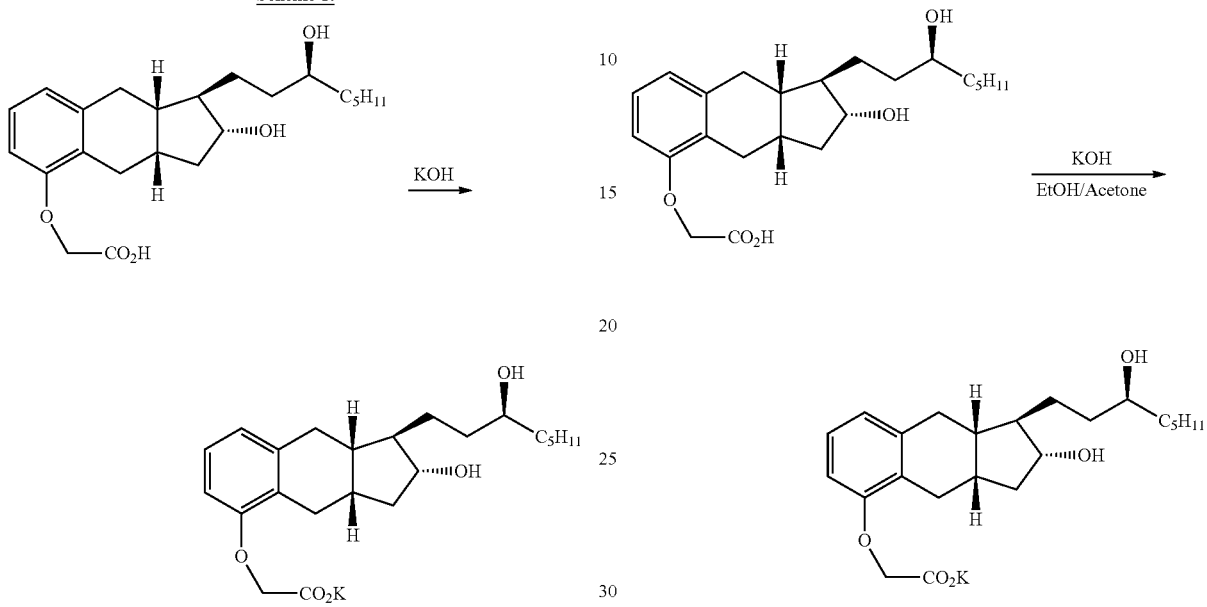

Part One: Condition Study

In this part of the experiment, UT-15 potassium salt was synthesized from two different solvent systems, ethanol/acetone and ethanol/ethyl acetate. The experiment was carried out with different ratios between ethanol and acetone, and between ethanol and ethyl acetate, to find the best solvent condition for the reaction.

a. Ethanol and Acetone

Figure 2:
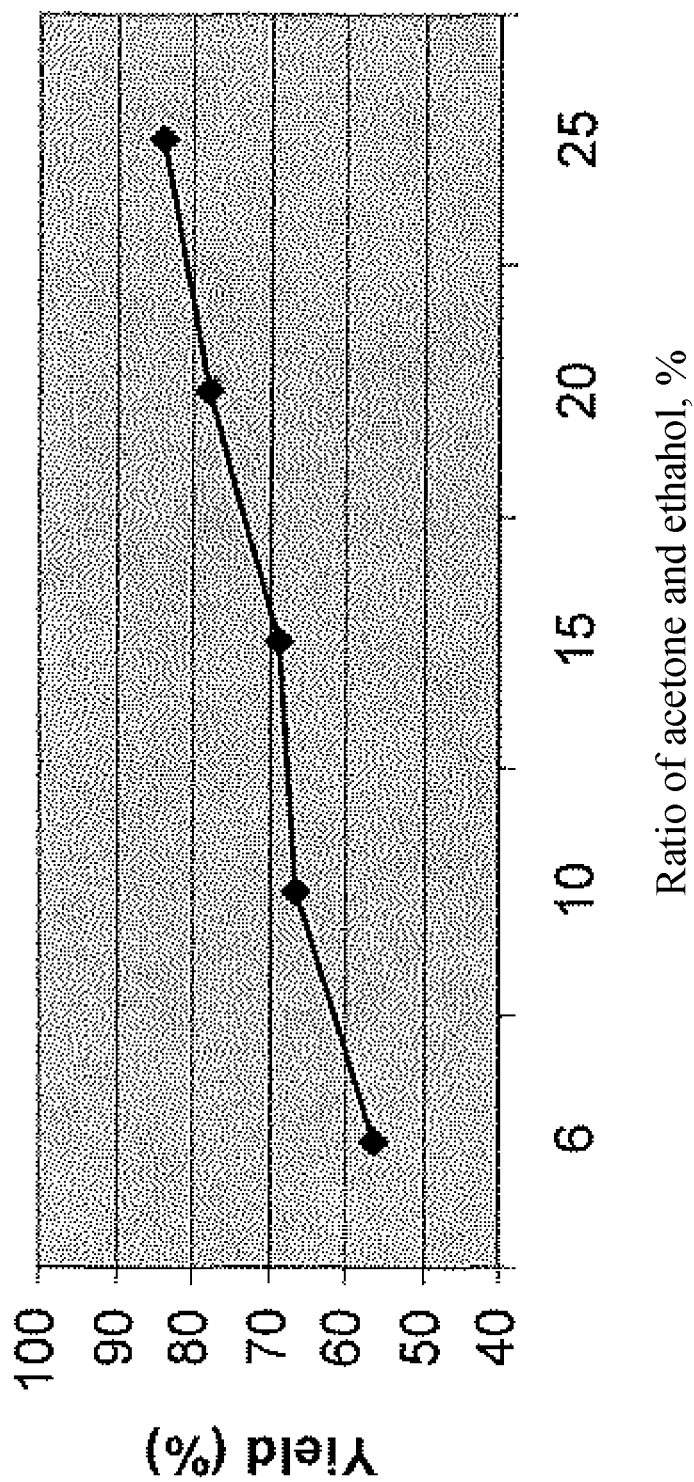
FIG. 2 is chart representing the relationship between yield and the acetone/ethanol ratio.

To a clear solution of potassium hydroxide (1 eq.) in ethanol (5 mL) in a round bottom flask, was added UT-I5 (1 eq.). The mixture was stirred at room temperature for about 10 minutes until a clear solution was obtained. Then acetone was added to the ethanol solution while stirring. The stirring was stopped when white solid started coming out from the solution. The mixture was left at room temperature overnight. The solid was collected by filtration. It was washed with acetone and then dried at 70° C. under vacuum for 4 hours. See the detail results in Table 1 and in FIG. 2.

TABLE 1

| | Results of UT-15 potassium salt in ethanol and acetone | | | | |
|---|---|---|---|---|---|
| Lot # | UT-15/KOH | Eq. | Acetone/EtOH | M.P. ° C. | Yield, % |
| D-1026-046 | 0.812 g/0.117 g | 1.0/1.0 | 30 mL/5 mL (6/1) | 178.5-179.5 | 56.1 |
| D-1026-047 | 0.710 g/0.102 g | 1.0/1.0 | 50 mL/5 mL (10/1) | 178.0-179.0 | 66.7 |
| D-1026-049 | 0.853 g/0.122 g | 1.0/1.0 | 75 mL/5 mL (15/1) | 177.8-179.0 | 68.4 |
| D-1026-051 | 0.723 g/0.104 g | 1.0/1.0 | 100 mL/5 mL (20/1) | 179.0-180.2 | 78.1 |
| D-1026-085 | 0.730 g/0.105 g | 1.0/1.0 | 125 mL/5 mL (25/1) | 179.0-181.0 | 83.6 | b. In Ethanol and Ethyl Acetate

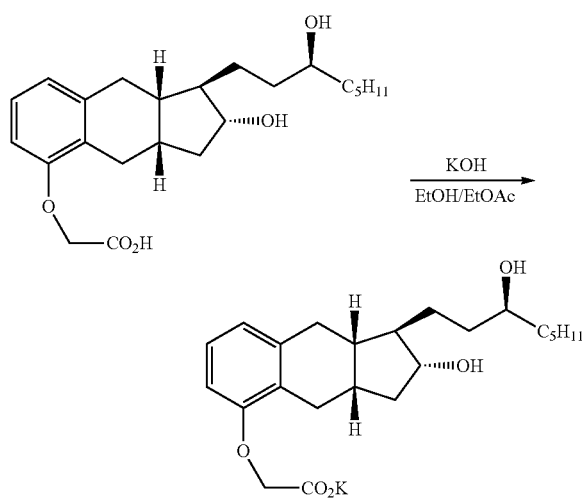

Figure 3:
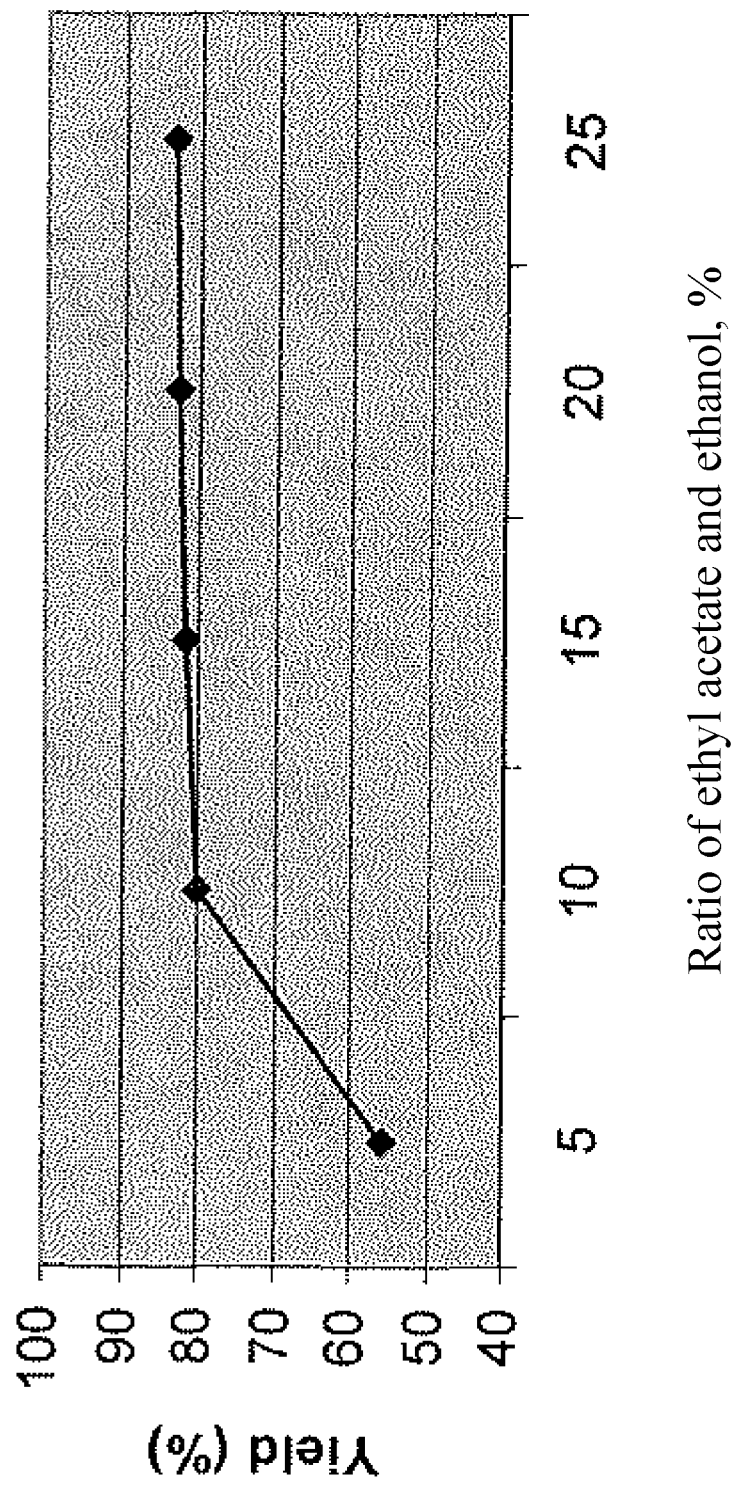
FIG. 3 is chart representing the relationship between yield and the ethyl acetate/ethanol ratio.

To a clear solution of potassium hydroxide (1 eq.) in ethanol (5 mL) in a round bottom flask, was added UT-15 (1 eq.). The mixture was stirred at room temperature for about 10 minutes until a clear solution was obtained. Then ethyl acetate was added to the ethanol solution while stirring. The stirring was stopped when white solid started coming out from the solution. The mixture was left at room temperature overnight. The solid was collected by filtration. It was washed with ethyl acetate and then dried at 70° C. under vacuum for 3 hours. See the detail results in Table 2 and in FIG. 3.

TABLE 2

Results of UT-15 potassium salt in ethanol and ethyl acetate

| Lot # | UT-15/KOH | Eq. | EtOH/Ethyl Acetate | M.P. ° C. | Yield, % |
|---|---|---|---|---|---|
| D-1026-056 | 0.870 g/0.125 g | 1.0/1.0 | 5 mL/25 mL (1/5) | 177.0-178.5 | 55.5 |
| D-1026-059 | 0.799 g/0.115 g | 1.0/1.0 | 5 mL/50 mL (1/10) | 179.5-180.8 | 79.8 |
| D-1026-062 | 0.771 g/0.111 g | 1.0/1.0 | 5 mL/75 mL (1/15) | 178.5-180.0 | 81.5 |
| D-1026-086 | 1.100 g/0.158 g | 1.0/1.0 | 5 mL/100 mL (1/20) | 179.0-180.5 | 82.8 |
| D-1026-087 | 0.998 g/0.143 g | 1.0/1.0 | 5 mL/125 mL (1/25) | 179.1-180.2 | 83.1 |

Part Two: Preparation of Treprostinil (UT-15) Potassium Salt (40 g Scale)

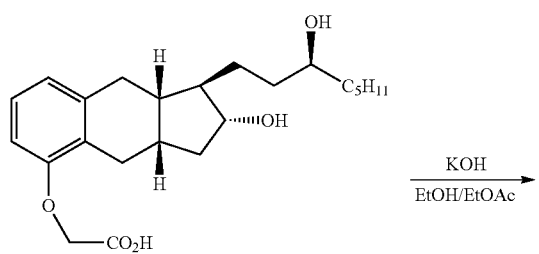

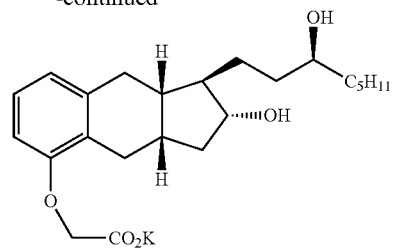

Table 3 provides materials used in the synthesis:

TABLE 3

| Reagents | MW | Amount | Mole | Eq. |
|---|---|---|---|---|
| UT-15 | 390.52 | 40.23 g | 0.103 | 1.00 |
| KOH | 56.11 | 5.78 g | 0.103 | 1.00 |
| Ethanol | — | 250 mL | — | — |
| Ethyl Acetate | — | 2500 mL | — | — |

To a 5-L round bottom flask, potassium hydroxide and ethanol were added. It was stirred at room temperature until it was clear. To the potassium ethanol solution, was added UT-15.

The reaction mixture was stirred at room temperature about 30 minutes until it was clear. The mixture was then added ethyl acetate slowly while stirring. The stirring was stopped when white solid started to come out of the solution. The reaction mixture was allowed at room temperature overnight. The solid was filtered, washed with ethyl acetate (500 mL), dried at 70° C. under vacuum for 6 hours to give the product (35.12 g, 79.5%).

Table 4 presents analytical data.

TABLE 4

| Melting point | 180.0-182° C. |
|---|---|
| IR | Consistent with Structure |
| $^1$H NMR | Consistent with Structure |
| $^{13}$C NMR | Consistent with Structure |
| Purity (HPLC) | 99.1% |
| Elemental Analysis | |

| | Carbon | Hydrogen |
|---|---|---|
| | 66.47% (Found) | 7.75% (Found) |
| | 66.45% *Theory) | 7.76% (Theory |

Example 2: UT-15-Calcium Salt and Tromethamine Salts

Summary. The objective of was to develop synthetic methods for the synthesis of new salts of UT-15 and produce at least 50 g of each salt. Present report describes the synthesis of two new salts of UT-15: calcium and tromethamine salts. For these new salts, analytical data: $^1$H-NMR, 13C-NMR, IR, purity by HPLC, DSC data, TGA data, water contents, specific rotation were collected.

Treprostinil (UT-I5) is benzindene prostacyclin containing carboxylic acid moiety. Various bases (organic and inorganic) were considered for the synthesis of new salts of UT-15. Present report uses two bases: calcium hydroxide (inorganic base) and tromethamine (organic base). Synthesis of these salts is a two step process. First step involved the reaction of UT-IS (carboxylic acid moiety) and base in appropriate solvent system, and second step was the recrystallization of salt from appropriate solvent system. Details of these steps are given in experimental section.

Calcium Salt

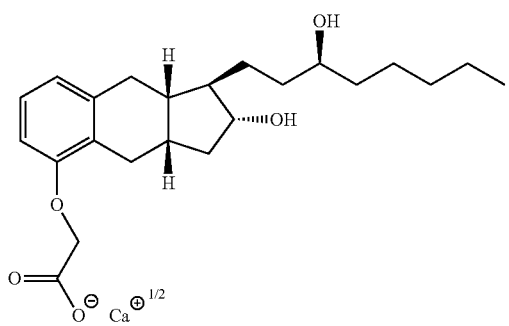

TABLE 5

Summary of materials used for synthesis of UT-15 calcium salt.

| Name | MW | Amount | Eq |
|---|---|---|---|
| UT-15 | 390.52 | 60 g | 1 |
| Calcium hydroxide | 74 | 5.40 | 0.5 |
| EtOH | — | 600 mL | — |
| Water | — | 1800 mL | — |

A 3000-mL, three-necked, round-bottom flask equipped with a mechanical stirrer, thermometer and condenser was charged with UT-15 (60 g), and ethanol (600 mL). Mixture was heated at 75-80° C. until clear. To the clear solution calcium hydroxide (5.40 g) was added in two portions. The reaction mixture was stirred and heated to 70-80° C. to obtain a clear solution (~1 h). Water (1800 mL) was added slowly keeping the temperature of solution at 75-80° C. After complete addition of water, the solution was allowed to cool to ambient temperature overnight while stirring. The product was filtered, washed with water and dried under vacuo for 1 h. The product was transferred from the Buchner funnel to a glass and dried over night in a fume hood. Finally the product was further dried under high vacuum at 50-55° C. for 6 hours (50.2 g, mp. 154-160° C.

Table 6 provides data for calcium salt.

TABLE 6

Structure

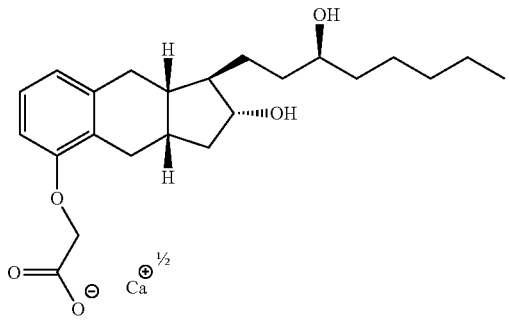

| | |
|---|---|
| Amount | 50 g |
| Lot number | D-1055-077-1 |
| Molecular formula | $C_{46}H_{68}CaO_{11}$ |
| MW | 837.12 |
| Appearance | Off white |
| $^1$H NMR | Consistent with structure |
| $^{13}$C NMR | Consistent with structure |
| Purity (HPLC) | 98.9% |
| Melting point | 154-160° C. |

Tromethamine Salt

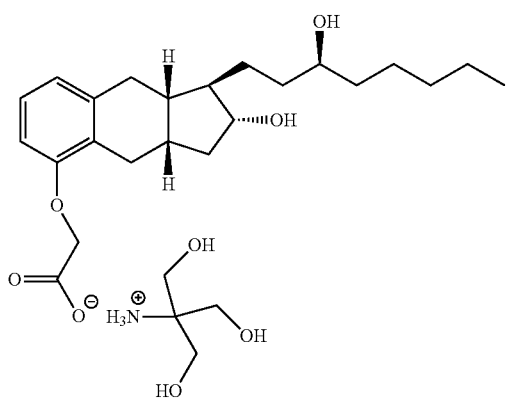 [SMILES: CCCCC[C@H](O)CC[C@@H]1[C@H]2Cc3cccc(OCC(=O)[O-])c3C[C@H]2C[C@H]1O ; [NH3+]C(CO)(CO)CO]

A 3000-mL, three-necked, round-bottom flask equipped with a mechanical stirrer, thermometer and condenser was charged with UT-15 (54.55 g), isopropanol (330 mL), and water (15 mL) and was heated at 50-55° C. until clear solution was obtained, then tromethamine (17.06 g) was added. The reaction mixture was heated to 60° C. while stirring to obtain a clear solution. To his clear solution methyl t-butyl ether (MTBE) was added slowly keeping the temperature between 50-55° C. After complete addition of MTBE, the solution was allowed to cool to ambient temperature overnight while stirring. The product was filtered, washed with water and dried under vacuo for 1 h. The product was transferred from the Buchner funnel to a glass tray and dried over night in a fume hood. Finally the product was dried under high vacuum at 45-48° C. for 4 hours (55.4 g, mp. 68-71° C.). Table 8 provides data for tromethamine salt.

TABLE 8

| | |
|---|---|
| Structure | (structure shown) |
| Amount | 50 g |
| Lot number | D-1051-023 |
| Molecular Formula | $C_{27}H_{45}NO_8$ |
| Molecular Weight | 511.66 |
| Appearance | White Solid |
| $^1$HNMR | Consistent with structure |
| $^{13}$C NMR | Consistent with structure |
| Purity (HPLC) | 99.93% |
| Melting point | 66-71° C. |
| Elemental analysis | Required C = 63.38, H = 8.86, N = 2.74 |
| | Required if as monohydrate: C = 61.23, H = 8.94, N = 2.64 |
| | Found: C = 60.54, H = 8.98, N = 2.63 |
| Water content | 4.4% w/w |
| Specific rotation | +32.4° @589 nm and 25° C. |
| | c = 1.0256 g/100 mL in MeOH |

TABLE 7

Summary of materials used for synthesis of UT-15 tromethanine salt.

| Name | MW | Amount | Eq |
|---|---|---|---|
| UT-15 | 390.52 | 54.55 g | 1.00 |
| Tromethanine | 121.14 | 17.06 | 1.00 |
| Isopropanol (IPA) | — | 330 mL | — |
| MTBE | — | 1500 mL | — |
| Water | — | 15 mL | — |

Example 3: Synthesis of Alternate Treprostinil Salts

The objective was to develop new methods for the synthesis of alternate salts of UT-15 and to produce at least 200 mg of each salt for the dissolution studies. Total seven salts of UT-15 have been prepared:
1. UT-15-L-Arginine salt
2. UT-15-L-Lysine salt
3. UT-15-N-Methylglucamine salt
4. UT-15-Choline salt
5. UT-15-Potassium salt
6. UT-15-Magnesium salt
7. UT-15-Ammonium salt For all new UT-15 salts, analytical data: IH-NMR, 13C_NMR, IR, purity by HPLC, DSC data, TGA data, water contents, specific rotation were collected.

Since UT-15 is benzindene prostacyclin containing carboxylic acid, various bases were considered for the synthesis of new salts of UT-15. This study used UT-15 with seven bases, which include four organic bases and three inorganic bases. Four organic bases were: L-arginine, L-lysine, N-methyl-glucamine, and choline hydroxide. Other three inorganic bases include potassium hydroxide, ammonia gas, and magnesium hydroxide. Synthesis of salts was a two step process. First step was the reaction of UT-15 (carboxylic acid) and base in appropriate solvent system, and second step. was the recrystallization of salt from appropriate solvent system. In some cases, the solvent system for both reaction step and recrystallization step was same, but in other cases it was different. Details of these steps were given in experimental section. In few cases, the purpose of addition of small amount of water was to avoid synthesis of ester of UT-15 with alcoholic solvent, when the mixture was heated to greater than 50° C.

Arginine Salt

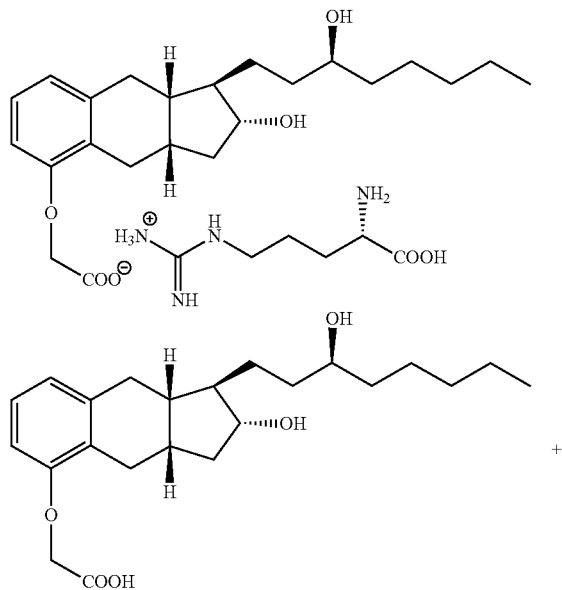

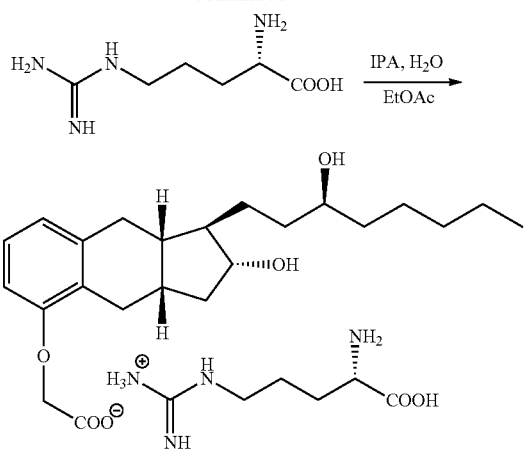

| Name | MW | Amount | Eq |
|---|---|---|---|
| UT-15 | 390.52 | 4.50 g | 1.00 |
| L-Arginine | 174.20 | 2.01 g | 1.00 |
| 2-propanol | — | 135 mL | — |
| Water | — | 10 mL | — |
| Ethyl Acetate | — | 250 mL | — |

Table 9 provides a summary of materials used in the synthesis.

A 500-mL, two-necked, round-bottom flask equipped with a magnetic stirrer, and a thermometer was charged with UT-15-L-Arginine salt (17.01 g), ethanol (200 mL). The mixture was heated to 70-80° C. while stirring. At this temperature, water (3 mL) was added slowly to obtain a clear solution. After complete addition of water, the solution was allowed to cool slowly to ambient temperature. The product was isolated by filtration and washed with ethanol. The product was transferred from the Buchner funnel to a glass container for air-drying over night in a fume hood. The product (lot D-1041-011) was dried under high vacuum at 70-75° C. for 16 hours. Table 10 provides data for the arginine salt.

TABLE 10

Structure

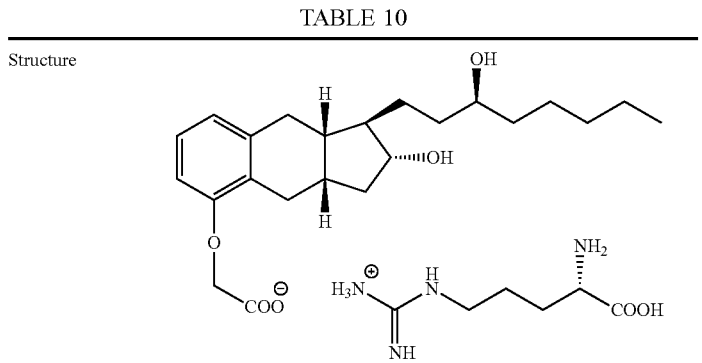

Lot number  D-1029-034
Molecular formula  $C_{29}H_{48}N_4O_7$
MW  564.72
Appearance  White Solid

TABLE 10-continued

| | |
|---|---|
| ¹H-NMR | Consistent with structure |
| ¹³C-NMR | Consistent with structure |
| Purity (HPLC) | 99.12% |
| Melting Point | 183-184° C. |
| Melting point (DSC) | 182.04° C. |
| IR | Consistent with structure |
| Elemental analysis | Required: C = 61.68, H = 8.57, N = 9.92 |
| | Found: C = 61.31, H = 8.55, N = 9.62 |
| TGA | Moisture = 2.07, degradation beyond 200° C. |
| Water content | 0.53% w/w |
| Specific rotation | +35.8° @589 nm and 25° C. |

L-Lysine Salt

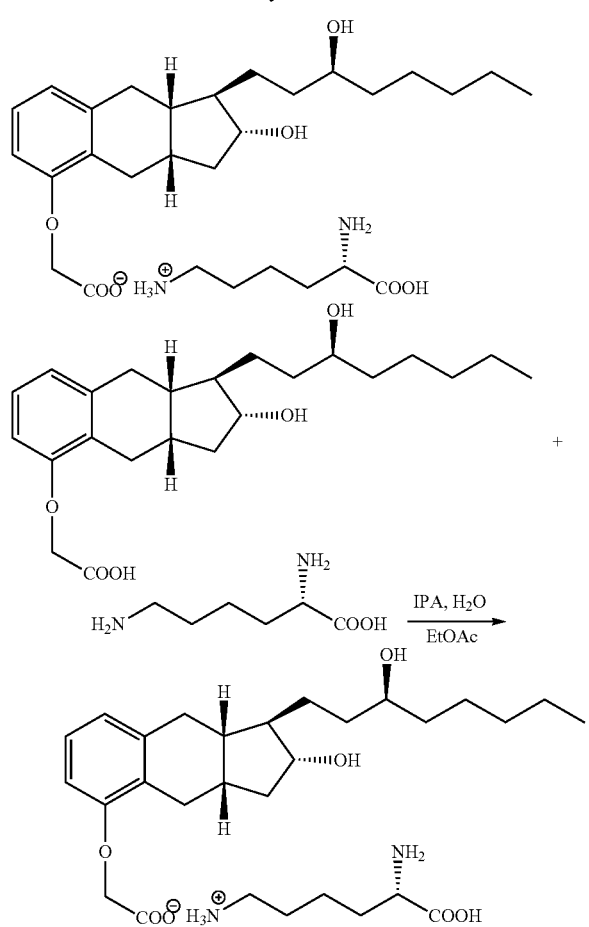

| Name | MW | Amount | Eq |
|---|---|---|---|
| UT-15 | 390.52 | 4.50 g | 1.00 |
| L-lysine | 146.19 | 1.685 g | 1.00 |
| 2-propanol | — | 108 mL | — |
| Water | — | 9 mL | — |
| Ethyl Acetate | — | 225 mL | — |

Table 11 provides summary of materials used in the synthesis

A 500-mL, two-necked, round-bottom flask equipped with a magnetic stirrer, and a thermometer was charged with UT-15 (4.5 g), 2-propanol (108 mL), water (9 mL), and L-lysine (1.685 g). The reaction mixture was stirred and heated to 70-80° C. to obtain a clear solution. At this temperature, ethyl acetate was added slowly keeping the temperature of solution higher than 55° C. After complete addition of ethyl acetate, the solution was allowed to cool to 45° C. during 1-2 hours, then to 35° C. for one hour, and then to 25° C. for an addition one hour. At ambient temperature, the product was isolated by filtration; product was washed with ethyl acetate. The product was transferred from Buchner funnel to a glass container for air-drying over night in a fume hood. The product was dried further under high vacuum at 50-55° C. for 4-5 hours. Table 12 provides data for L-lysine salt.

Structure

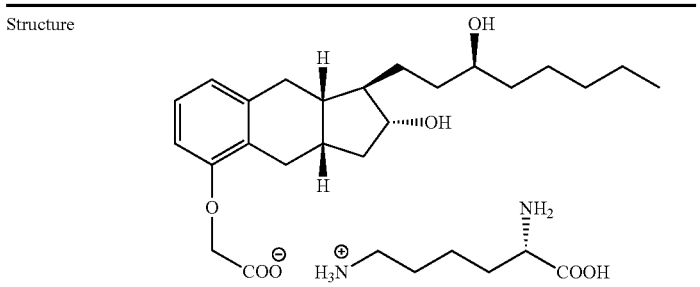

| | |
|---|---|
| Lot number | D-1029-032 |
| Molecular formula | $C_{29}H_{48}N_2O_7$ |
| MW | 536.71 |

| | |
|---|---|
| Appearance | White Solid |
| $^1$H-NMR | Consistent with structure |
| $^{13}$C-NMR | Consistent with structure |
| Purity (HPLC) | 99.68% |
| Melting Point | 106° C. |
| Melting point (DSC) | 97.43° C. |
| IR | Consistent with structure |
| Elemental analysis | Required: C = 64.90, H = 9.01, N = 5.22 |
| | Found: C = 60.90, H = 9.04, N = 4.85 |
| TGA | No weight loss due to moisture; loss due to degradation beyond 200° C. |
| Water content | 6.7% w/w |
| Specific rotation | +36.3° @589 nm and 25° C. |

N-Methylglucamine Salt

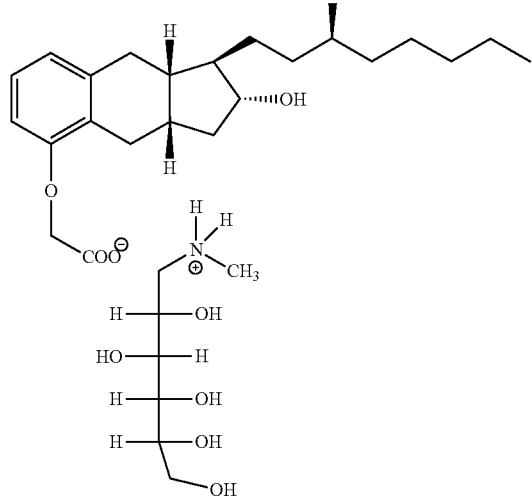

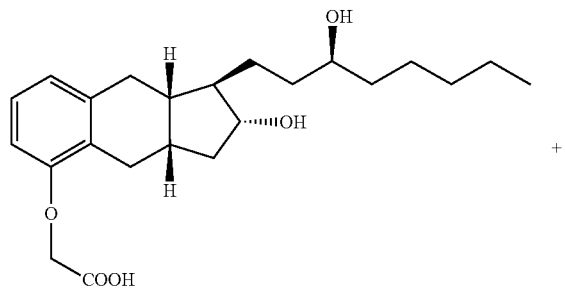

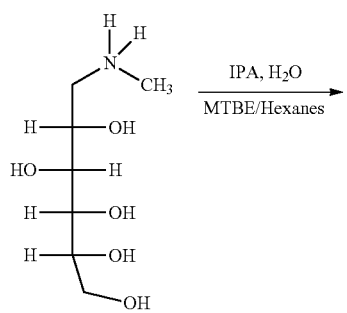

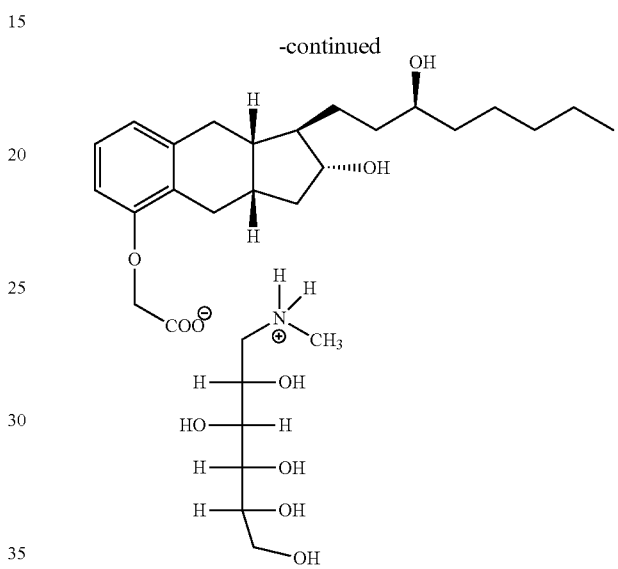

| Name | MW | Amount | Eq |
|---|---|---|---|
| UT-15 | 390.52 | 4.00 g | 1.00 |
| N-methylglucamine | 146.19 | 2.00 g | 1.00 |
| 2-propanol | — | 60 mL | — |
| Water | — | 0.8 mL | — |
| MTBE | — | 120 mL | — |
| Hexanes | — | 40 mL | — |

Table 13 provides a summary of materials used in the experiments

A 500-mL, two-necked, round-bottom flask equipped with a magnetic stirrer, and a thermometer was charged with UT-15 (4.0 g), 2-propanol (108 mL), water (0.8 mL), and N-methylglucamine (2.00 g). The reaction mixture was stirred and heated to 70-80° C. to obtain a clear solution. At this temperature, MTBE (120 mL) was added slowly keeping the temperature of solution higher than 55° C., followed by hexanes (40 mL). After complete addition of MTBE and hexanes, the solution was allowed to cool to 45° C. during 1-2 hours, then to 35° C. for one hour, and then to 25° C. for an additional 30 minutes. At ambient temperature, the product was isolated by filtration and washed with MTBE/hexanes (1:1). The product was transferred from Buchner funnel to a glass container for air-drying over night in fume hood. The product was dried further under vacuum at 50-55° C. for 4 hours. Table 14 provides results for N-methylglucamine salt.

TABLE 14

Structure

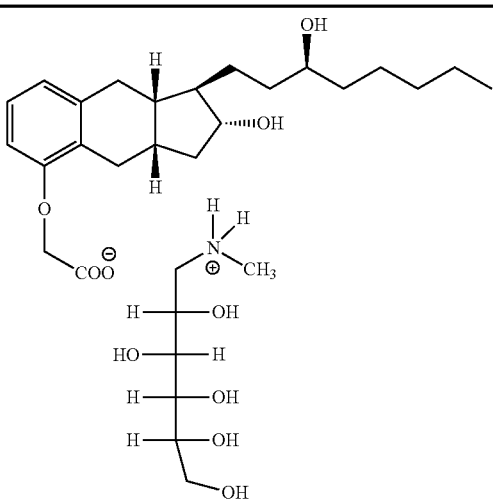

| | |
|---|---|
| Lot number | D-1029-036 |
| Molecular formula | $C_{30}H_{51}NO_{10}$ |
| MW | 585.74 |
| Appearance | White Solid |
| $^1$H-NMR | Consistent with structure |
| $^{13}$C-NMR | Consistent with structure |
| Purity (HPLC) | 99.51% |
| Melting Point | 82-83° C. |
| Melting point (DSC) | 72.96° C. |
| IR | Consistent with structure |
| Elemental analysis | Required: C = 61.52, H = 8.78, N = 2.39 |
| | Found: C = 59.77, H = 8.78, N = 2.34 |
| TGA | Weight loss due to moisture up to 100° C.; loss due to degradation beyond 150° C. |
| Water content | 3.3% w/w |
| Specific rotation | +19.4° @589 nm and 25° C. |

Mg Salt

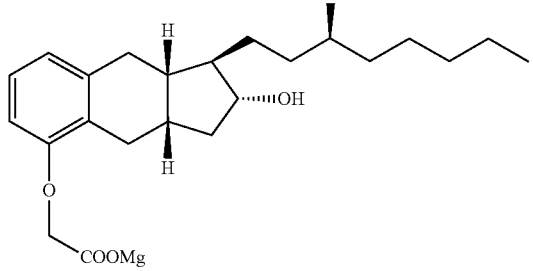

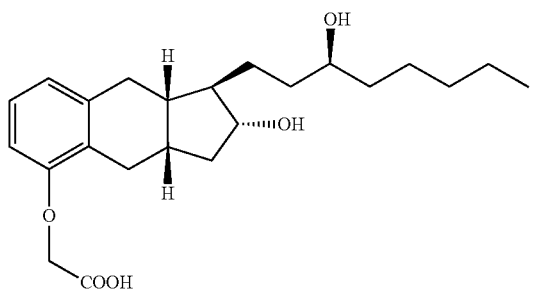

+

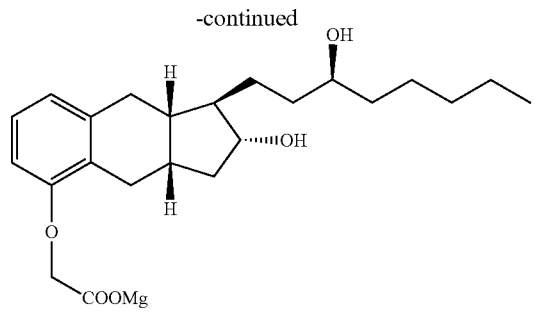

| Name | MW | Amount | Eq |
|---|---|---|---|
| UT-15 | 390.52 | 5.75 g | 1.00 |
| Magnesium Hydroxide | 58.33 | 0.439 g | 0.5 |
| Ethanol | — | 172 mL | — |
| Water | — | 55 mL | — |
| MTBE | — | 86 mL | — |
| Hexanes | — | 30 mL | — |

Table 15 provides summary of materials used in the experiment.

A 500-mL, two-necked, round-bottom flask equipped with a magnetic stirrer, and a thermometer was charged with UT-15 (5.75 g), ethanol (86 mL), water (55 mL), and magnesium hydroxide (439 mg). The reaction mixture was stirred and heated to 70-80° C. to obtain a clear solution. The solution was filtered to remove any insoluble foreign particles. The filtrate was evaporated under vacuum to give a gummy material. The gummy material was dissolved in ethanol (86 mL) by heating to 70-80° C. At this temperature, MTBE (86 mL) was added slowly keeping the temperature of solution higher than 55° C., followed by hexanes (30 mL). After complete addition of MTBE and hexanes, the solution was allowed to cool to 45° C. during 1-2 hours, then to ambient temperature overnight. At ambient temperature, the product was isolated by filtration and washed with MTBE. The product was transferred from Buchner funnel to a glass container for air-drying over night in fume hood. The product was dried further under vacuum at 50-55° C. for 4 hours. Table 16 provides data for the magnesium salt.

TABLE 16

Structure

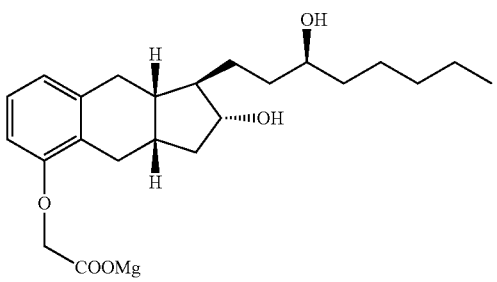

| | |
|---|---|
| Lot number | D-1029-038 |
| Molecular formula | $C_{23}H_{33}MgO_5$ |
| MW | 413.82 |
| Appearance | White Solid |
| $^1$H-NMR | Consistent with structure |
| $^{13}$C-NMR | Consistent with structure |
| Purity (HPLC) | 99.68% |
| Melting Point | 80-81.5° C. |
| Melting point (DSC) | 75.77° C. |
| IR | Consistent with structure |
| Elemental analysis | Required: C = 66.76, H = 8.04 |
| | Found: C = 66.90, H = 8.29 |
| TGA | No weight loss due to moisture; loss due to degradation beyond 250° C. |
| Water content | 13.1% w/w |
| Specific rotation | +44° @589 nm and 25° C. |

Potassium Salt

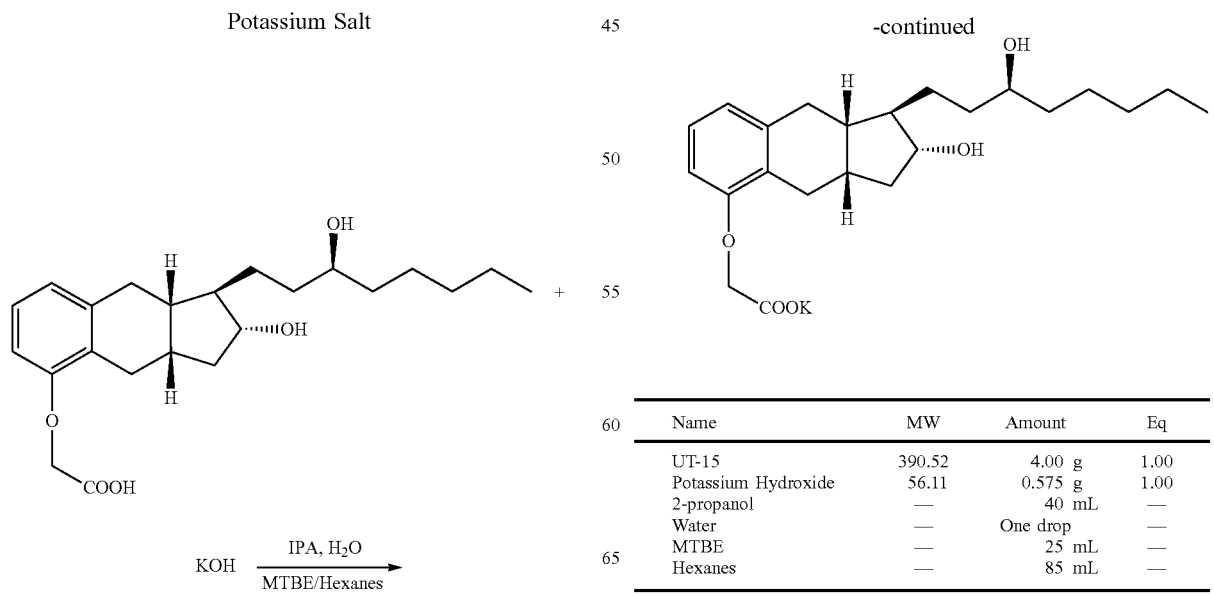

| Name | MW | Amount | Eq |
|---|---|---|---|
| UT-15 | 390.52 | 4.00 g | 1.00 |
| Potassium Hydroxide | 56.11 | 0.575 g | 1.00 |
| 2-propanol | — | 40 mL | — |
| Water | — | One drop | — |
| MTBE | — | 25 mL | — |
| Hexanes | — | 85 mL | — |

Table 17 provides a summary of materials used in the experiment.

A 500-mL, two-necked, round-bottom flask equipped with a magnetic stirrer, and a thermometer was charged with UT-15 (4.00 g), 2-propanol (40 mL), water (one drop), and potassium hydroxide (575 mg). The reaction mixture was stirred and heated to 70-80° C. to obtain a clear solution. At this temperature, MTBE (25 mL) was added slowly keeping the temperature of solution higher than 55° C., followed by hexanes (85 mL). After complete addition of MTBE and hexanes, the solution was allowed to cool to 45° C. during approximately 16 hours, then to ambient temperature. At ambient temperature, the product was isolated by filtration and washed with MTBE. The product was transferred from Buchner funnel to a glass dish for air-drying overnight in fume hood. The product (lot D-1 029-041) was dried further under vacuum at 50-55° C. for 4 hours. Table 18 provides data for the potassium salt.

TABLE 18

Structure

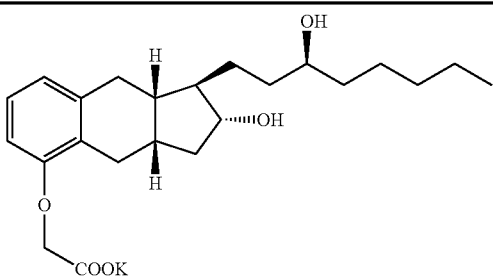

| | |
|---|---|
| Lot number | D-1029-041 |
| Molecular formula | $C_{23}H_{33}KO_5$ |
| MW | 428.61 |
| Appearance | White Solid |
| $^1$H-NMR | Consistent with structure |
| $^{13}$C-NMR | Consistent with structure |
| Purity (HPLC) | 99.39% |
| Melting Point | 180-181° C. |
| Melting point (DSC) | 177.37° C. |
| IR | Consistent with structure |
| Elemental analysis | Required: C = 64.45, H = 7.76 |
| | Found: C = 64.42 H = 7.77 |
| TGA | No weight loss due to moisture; loss due to degradation beyond 250° C. |
| Water content | 0.3% w/w |
| Specific rotation | +39.5° @589 nm and 25° C. |

Ammonium Salt

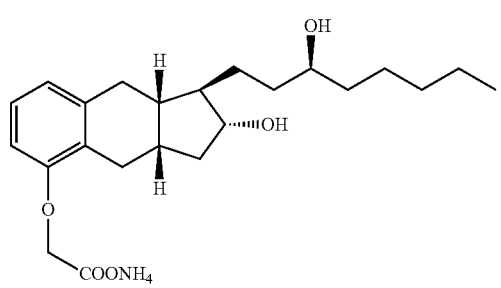

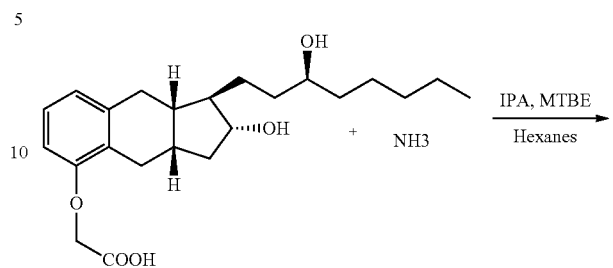

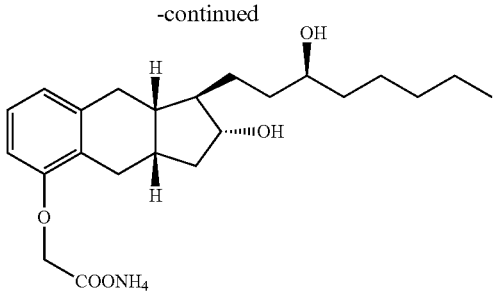

| Name | MW | Amount | Eq |
|---|---|---|---|
| UT-15 | 390.52 | 4.00 g | 1.00 |
| Ammonia (gas) | 17.03 | — | — |
| 2-propanol | — | 50 mL | — |
| MTBE | — | 75 mL | — |
| Hexanes | — | 75 mL | — |

Table 19 provides summary of materials used in the experiment

A 500-mL, two-necked, round-bottom flask equipped with a magnetic stirrer, and a thermometer was charged with UT-15 (4.00 g), 2-propanol (40 mL). The mixture was stirred and heated to 40-45° C. to obtain a clear solution. Allow the temperature of the solution to cool to 30-35° C., and then bubble the ammonia gas through the solution for 45 minutes. Ammonia gas inlet was removed, and hexane (75 mL) was added and allowed the mixture to stir overnight at ambient temperature. At ambient temperature, the product was isolated by filtration; product was washed with MTBE/hexanes (1:1). The product was transferred from Buchner funnel to a glass dish for air-drying over night in fume hood. The product (lot D-1029-043) was dried further under vacuum at 50-55° C. for 4 hours. Table 20 provides data for the ammonium salt.

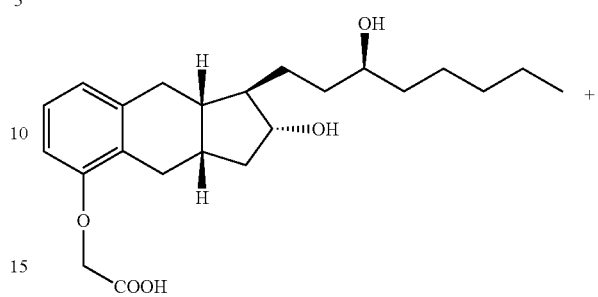

TABLE 20

Structure

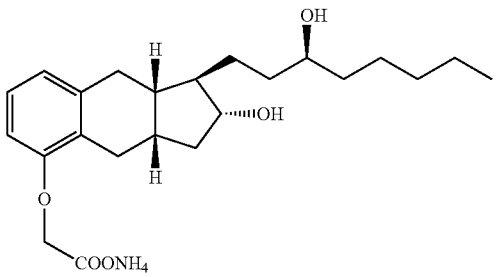

| | |
|---|---|
| Lot number | D-1029-043 |
| Molecular formula | $C_{23}H_{37}NO_5$ |
| MW | 407.55 |
| Appearance | White Solid |
| $^1$H-NMR | Consistent with structure |
| $^{13}$C-NMR | Consistent with structure |
| Purity (HPLC) | 99.52% |
| Melting Point | 75-76° C. |
| Melting point (DSC) | 69.42° C. |
| IR | Consistent with structure |
| Elemental analysis | Required: C = 67.78, H = 9.15, N = 3.44 |
| | Found: C = 67.24, H = 9.13, N = 2.76 |
| TGA | 4% weight loss due to moisture up to 100° C.; continuous loss due to degradation beyond 100° C. |
| Water content | 4.6% w/w |
| Specific rotation | +41.4° @589 nm and 25° C. |

Choline Salt

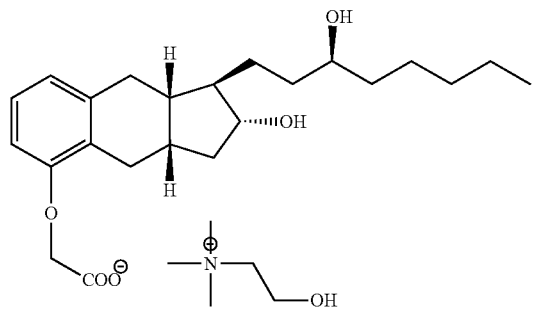

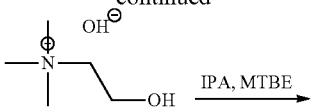

-continued

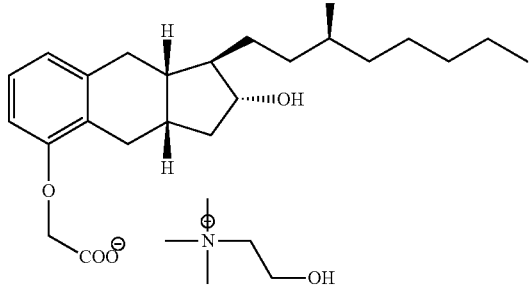

| Name | MW | Amount | Eq |
|---|---|---|---|
| UT-15 | 390.52 | 4.00 g | 1.00 |
| Choline hydroxide (45% wt, MeOH) | 121.18 | 3.1 g | 1.0 |
| 2-propanol | — | 60 + 90 mL | — |
| MTBE | — | 115 mL | — |

Table 21 provides summary of materials used in the experiment.

A 500-mL, two-necked, round-bottom flask equipped with a magnetic stirrer, and a thermometer was charged with UT-15 (4.50 g), 2-propanol (60 mL). The mixture was stirred and heated to 70-80° C. to obtain a clear solution. To the solution was added choline hydroxide (3.1 g) and stirred the mixture for short period. The solvent was evaporated under vacuum to give a gummy material. The gummy material was dissolved in 2-propanol (90 mL) by heating to 70-80° C. At this temperature, MTBE (115 mL) was added slowly keeping the temperature of solution more than 55° C. After complete addition of MTBE, the solution was allowed to cool to 50° C., then to 40° C. and to ambient temperature overnight. At ambient temperature, the product was isolated by filtration; product was washed with MTBE/hexanes (1:1). The product was transferred from Buchner funnel to a glass container for air-drying over night in fume hood. The product was dried further under vacuum at 50-55° C. for 4 hours. Table 22 provides data for the choline salt.

Example 4: Synthesis of Potassium and L-Arginine Salts of Treprostinil

This example reports to the synthesis of two salts, potassium salt of UT-15 (UT-15D) and L-Arginine salt of UT-15. From synthetic point of view, the desired properties of UT-15 salts may include better aqueous solubility, higher melting point, dense nature, and robust process. Two salts, UT-15D and UT-15-L-Arginine possess the desired properties. Presently, potassium salt of UT-15 (UT-15D) was prepared using ethanol and ethyl acetate. Initially, Arginine salt of UT-15 was prepared and recrystallized using IPA/EtOAc/H$_2$O. Currently, IPA/H$_2$O and EtOH/H$_2$O solvent systems were used for recrystallization. The number of solvents for recrystallization was reduced (three to two). Ethanol is preferred over isopropanol for recrystallization, because isopropanol was not removed completely from UT-15-L-Arginine at temperature 70-75° C., under high vacuum for more than 45 hours, whereas ethanol was removed within 16 hours under similar conditions.

Potassium Salt

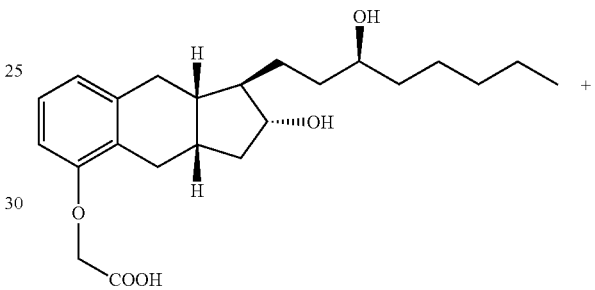

TABLE 22

Structure

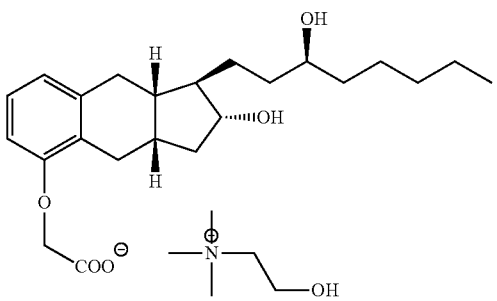

| | |
|---|---|
| Lot number | D-1029-045 |
| Molecular formula | C$_{28}$H$_{47}$NO$_6$ |
| MW | 493.68 |
| Appearance | White Solid |
| $^1$H-NMR | Consistent with structure |
| $^{13}$C-NMR | Consistent with structure |
| Purity (HPLC) | 99.36% |
| Melting Point | 163-164 °C. |
| Melting Point (DSC) | pending° C. |
| IR | Consistent with structure |
| Elemental analysis | Required: C = 68.12, H = 9.60, N = 2.84<br>Found: C = 67.76, H = 9.69, N = 2.83 |
| TGA | No weight loss due to moisture; loss due to degradation beyond 150° C. |
| Water content | 0.9% w/w |
| Specific rotation | +34.2° @589 nm and 25° C. |

-continued

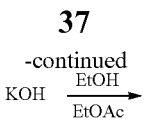

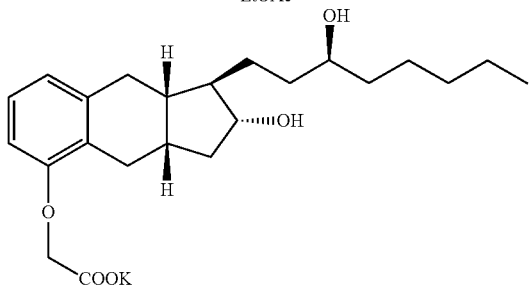

| Name | MW | Amount | Eq | Ratio |
|---|---|---|---|---|
| UT-15 | 390.52 | 150.00 g | 1.00 | 1.00 |
| Potassium hydroxide | 56.11 | 21.55 g | 1.00 | NA |
| Ethyl acetate | NA | 7500 mL | NA | 50.00 |
| Ethanol | NA | 115 mL | NA | 5.00 |

Table 23 provides summary of materials used for the potassium salt synthesis.

A 12-L, three-necked, round-bottom flask equipped with a mechanical stirrer was charged with potassium hydroxide (21.55 g), ethanol (650 mL) at room temperature. The mixture was stirred to obtain a clear solution. UT-15 (150.00 g, solid) was added in portions to the solution of potassium hydroxide in ethanol at ambient temperature. After complete addition of UT-15, the mixture was stirred for 30 minutes to obtain a clear solution. At ambient temperature, ethyl acetate (7500 mL) was added solution slowly keeping the solution clear. The clear solution was allowed to stir gently at ambient temperature for 3-4 hours to obtain a white solid. The product was isolated by filtration and washed with ethyl acetate. The product was transferred from the Buchner funnel to a glass tray and air-dried in a fume-hood overnight. The product (lot D-1029-171) was dried further under vacuum at 60-65° C. for 7-8 hours to give UT-15D (133.0 g, yield 81%) Table 24 provides data for potassium salt.

L-Arginine Salt

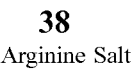

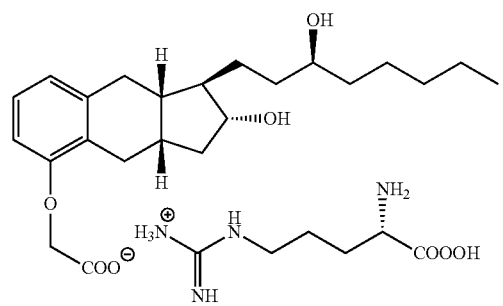

| Name | Amount | Ratio | Lot No. |
|---|---|---|---|
| UT-15-L-Arginine salt | 17.01 | 1.00 | D-1041-006 |
| Ethanol (anhydrous) | 200 mL | 11.76 | T-08-0186 |
| Water | 3 mL | 0.176 | Tap water |

Table 25 provides summary of materials used in the L-arginine salt synthesis.

A 500-mL, two-necked, round-bottom flask equipped with a magnetic stirrer, and a thermometer was charged with UT-15-L-Arginine salt (17.01 g), ethanol (200 mL). The mixture was heated to 70-80° C. while stirring. At this temperature, water (3 mL) was added slowly to obtain a clear solution. After complete addition of water, the solution was allowed to cool slowly to ambient temperature. The product was isolated by filtration and washed with ethanol. The product was transferred from the Buchner funnel to a glass container for air-drying over night in a fume hood. The product (lot D-1041-011) was dried under high vacuum at 70-75° C. for 16 hours. Table 26 provides data for the L-arginine salt.

TABLE 24

Structure

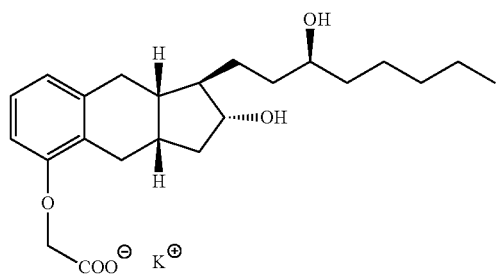

| | |
|---|---|
| Lot number | D-1029-166 |
| Molecular formula | $C_{23}H_{33}KO_5$ |
| MW | 428.61 |
| Appearance | White Solid |
| $^1$H-NMR | Consistent with structure |
| $^{13}$C-NMR | Consistent with structure |
| Purity (HPLC) | 99.9% |
| Melting Point | 182-183.5° C. |
| IR | Consistent with structure |

TABLE 26

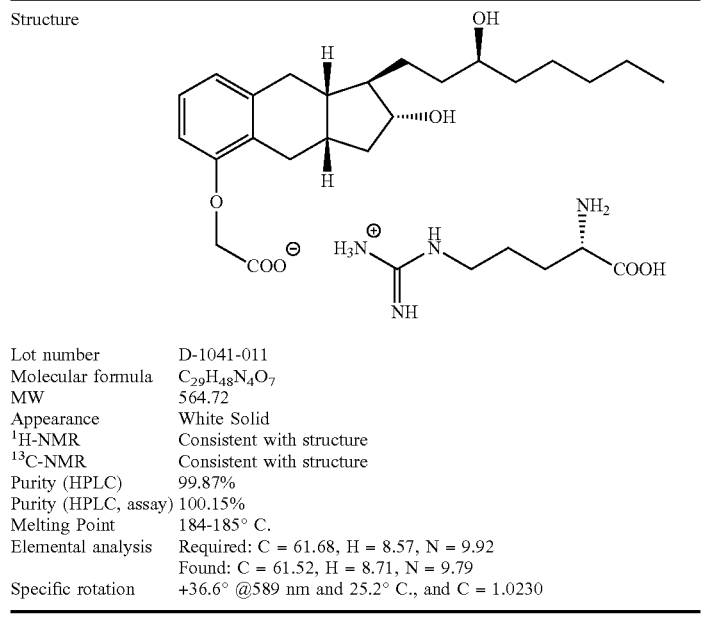

| | |
|---|---|
| Lot number | D-1041-011 |
| Molecular formula | $C_{29}H_{48}N_4O_7$ |
| MW | 564.72 |
| Appearance | White Solid |
| $^1$H-NMR | Consistent with structure |
| $^{13}$C-NMR | Consistent with structure |
| Purity (HPLC) | 99.87% |
| Purity (HPLC, assay) | 100.15% |
| Melting Point | 184-185° C. |
| Elemental analysis | Required: C = 61.68, H = 8.57, N = 9.92 |
| | Found: C = 61.52, H = 8.71, N = 9.79 |
| Specific rotation | +36.6° @589 nm and 25.2° C., and C = 1.0230 |

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of preparing a potassium salt of treprostinil comprising: reacting treprostinil with potassium hydroxide in a solution comprising ethanol and ethyl acetate to form the potassium salt of treprostinil, wherein a volume ratio of ethanol:ethyl acetate in the solution ranges from 1:25 to 1:5.

2. The method of claim 1, wherein the volume ratio of ethanol:ethyl acetate in the solution ranges from 1:25 to 1:10.

3. The method of claim 1, wherein the volume ratio of ethanol:ethyl acetate in the solution ranges from 1:15 to 1:10.

4. The method of claim 1, wherein the volume ratio of ethanol:ethyl acetate in the solution is 1:10.

5. The method of claim 1, wherein said reacting comprises contacting treprostinil with a solution of potassium hydroxide in ethanol followed by adding ethyl acetate.

6. The method of claim 1, further comprising stirring the solution until a solid starts coming out of the solution.

7. The method of claim 6, further comprising collecting the solid.

8. The method of claim 7, wherein said collecting is performed by filtrating the solution.

9. The method of claim 7, further comprising washing and drying the collected solid.

10. The method of claim 9, wherein said washing is washing with ethyl acetate.

11. The method of claim 9, wherein said drying is vacuum drying.

12. The method of claim 9, wherein the dried solid has a melting temperature ranging from 178.5° C. to 182.0° C.

13. The method of claim 10, wherein the dried solid has a melting temperature ranging from 179.5° C. to 180.8° C.

14. The method of claim 1, wherein a yield of said potassium salt is at least 79.8%.

15. The method of claim 1, wherein at least 35.12 g of the potassium salt of treprostinil is produced.

* * * * *